United States Patent
Hebrank et al.

(10) Patent No.: US 6,169,403 B1
(45) Date of Patent: Jan. 2, 2001

(54) METHOD AND MR DEVICE FOR SIMULATING ELECTRICAL SIMULATIONS IN A SUBJECT BY MR STIMULATION

(75) Inventors: Franz Hebrank, Hessdorf; Matthias Gebhardt, Erlangen; Helmut Lenz, Oberasbach, all of (DE)

(73) Assignee: Siemens Aktiengesellschaft, Munich (DE)

(*) Notice: Under 35 U.S.C. 154(b), the term of this patent shall be extended for 0 days.

(21) Appl. No.: 09/300,782

(22) Filed: Apr. 27, 1999

(30) Foreign Application Priority Data

Apr. 29, 1998 (DE) .............................................. 198 19 243
Mar. 25, 1999 (DE) .............................................. 199 13 547

(51) Int. Cl.$^7$ .................................................. G01V 3/00
(52) U.S. Cl. ........................................... 324/318; 324/309
(58) Field of Search .................................. 324/318, 309, 324/324, 300; 600/410, 407

(56) References Cited

U.S. PATENT DOCUMENTS 5,497,773 * 3/1996 Kuhara et al. ..................... 128/653.5

OTHER PUBLICATIONS

Werner Irnich et al, Magnetostimulation in MRI, article published in the journal od Magnetic Resonance Imaging, vol. 33:619–623 (1995).*

W. Irnich, Electrostimulation by time–varying magnetic fields, article published in MAGMA, vol. 2: 43–49 (1994).*

Joachim Abart et al, Peripheral Nerve Stimulation by Time–Varying Magnetic Fields, article published in the Journal of Computer Assiated Tomography, vol. 21:532–538 (1997).*

* cited by examiner

Primary Examiner—Christine K. Oda
Assistant Examiner—Brij B. Shrivastav
(74) Attorney, Agent, or Firm—Schiff Hardin & Waite

(57) ABSTRACT

A method or apparatus for the simulation of electrical stimulations in an examination subject which are generated by rapidly switched gradient fields of an MR device, and wherein aborting of the executed measuring sequence occurs given the crossing of a threshold value in an online monitoring, wherein the crossing of the threshold value is signaled prior to the execution of the measuring sequence in a look-ahead monitoring, at least one gradient signal G(t) is determined which is defined by the time characteristic of the gradient pulses, at least one first filtered gradient signal $G_{F1}(t)$ is formed by filtering the gradient signal G(t) with a first filtering function $f_{F1}(t)$ a stimulation signal Stim(t) is formed which describes the stimulation of the examination subject, from the first filtered gradient signal $G_{F1}(t)$, and the stimulation signal Stim(t) is compared to a definable stimulation threshold value $Stim_{lim}$. If $Stim_{lim}$ is exceeded an indicator indicating that a stimulation has occurred is emitted.

29 Claims, 15 Drawing Sheets

METHOD AND MR DEVICE FOR SIMULATING ELECTRICAL SIMULATIONS IN A SUBJECT BY MR STIMULATION

BACKGROUND OF THE INVENTION

1. Field of the Invention

The present invention relates to a method for simulating the electrical stimulations which are generated in an examination subject by gradient coils of an MR device.

2. Description of the Prior Art

In the known MR devices, rapidly switched gradient fields with a high amplitude are superimposed on a basic magnetic field.

In MR exams, the patients can be stimulated by switching the gradient impulses (known as MR stimulation). The stimulations are caused by the effect of an electrical field on the patient. The electrical field is induced by the alteration, according to Maxwell's equations, of the magnetic flux B which is generated by each of the three gradient coils. For a given MR device, the magnitude of the electrical field that is generated by switching a gradient coil is directly proportional to the time variation of the value of the magnetic flux B, expressed by dB/dt, i.e., the time derivative of the magnitude of the magnetic field which is produced by the gradient coil. Because of the proportionality of the electrical field and dB/dt (chronological change of the magnetic flux B), it is sufficient merely to observe the time variation of the magnetic flux B.

On the basis of the proportionality of the magnetic flux B and the gradient field G for a given gradient coil, monitoring the time variation d/dt of the spatially dependent gradient field G (in mT/m) is equivalent to aforementioned monitoring the time variation d/dt of the spatially dependent magnetic flux B (in mT). Therefore, the following considers the time variation of the gradient signals.

A stimulation occurs when a characteristic threshold value of the electrical field is exceeded. The corresponding threshold value of dB/dt, or of dG/dt, depends for a fixed gradient schema on the anatomy and the physiology of the patient, his orientation in the MR device and the geometric and physical properties of the three gradient coils. The value dB/dt is defined by the amplitude of the gradient pulses and the rise times. In practice, however, the gradient profile is not constant from pulse to pulse, either with respect to the amplitudes or the timing, but rather, besides being dependent on the selection of the measuring sequence, it depends in particular on the selected measuring parameters (e.g. slice thickness, number of slices, field of view FOV, matrix size, repetition time $T_R$, echo time $T_E$, etc.). In this case, in addition to the aforementioned parameters, the threshold value for the stimulation particularly depends on the time configuration of the individual gradient pulses, their total number and repetition rate, and the superimposition of all three gradient coils $G_x$, $G_y$, and $G_z$.

For whole-body gradient coils, not only the $B_z$ component of the magnetic field, which extends in a longitudinal direction, but also its transverse components $B_x$ and $B_y$ are responsible for the stimulation, the $B_y$ component being more critical with respect to stimulations, since the field lines penetrate the body frontally. Thus, given a prone or supine position of the patient, the stimulation limit value for the y-axis must be the smallest.

As an extreme simplification, from a physiological perspective, a consciously perceived stimulation by an external electrical field can be described in two steps. The electrical field can either act directly from outside or can be induced by a varying magnetic field.

In a first step, the electrical field generates an electrical potential at the cell wall of the stimulated nerve cells. The cell wall of the nerve cell can be approximately imagined as a capacitor which is charged by the electrical field. When the electrical potential exceeds a characteristic threshold, an action potential is triggered in the nerve cell and spreads over the entire nerve cell.

In the second step, at the connection of two nerve cells (a synapse), an action potential on the presynaptic side leads to a diffusion out of chemical messenger substances. These substances are absorbed on the postsyanptic side, i.e., they are absorbed in the nerve cell which is connected downstream, where they trigger another action potential. The stimulus spreads. The concentration of the messenger substances in the synapse is a measure of the number of postsynaptically triggered action potentials. In particular, the concentration of the messenger substances in the synapse subsides only gradually. The characteristic time constant is in the range of a few milliseconds. A more exact description of the neurophysiological processes can be found in the text *Neuro-und Sinnesphysiologie* (R. F. Schmidt, pub.; Springer, Second Edition 1995: Chapters 2 and 3).

In order to avoid such stimulations in the examined body given rapidly switched gradient fields of high amplitude, it is taught in German OS 42 25 592 to cover, with a closed conductor loop, those regions outside the examination region which are sensitive to stimulation. This results in a reduction of the currents induced in the covered region. This method is based on the fact that, given switched gradients, the highest current values are induced outside the examination region, so that the danger of stimulations is greatest there. The linearity of the gradients in the examination region, which is of importance for the image quality, is minimally compromised by the attachment of conductor loops outside the examination region. Given a change of examination region, however, the position of the conductor loops must also be adjusted.

There are also known methods which enable a prediction of magnetostimulations. One of these approaches to stimulation monitoring is what is known as the dB/dt model. This method involves checking and monitoring the pure dB/dt values that arise in a measurement. The maximum permissible dB/dt values derive from the result of a stimulation study with the corresponding gradient coil, or from the limit values which are strictly prescribed by the certification authorities. Further details can be from in the article "Peripheral Nerve Stimulation by Time-Varying Magnetic Fields" (J. Abart, *J. Computer Assisted Tomography* (1997); 21(4):532–38. The dB/dt model does not adequately consider the patient physiology; in particular, the dependency of the stimulation threshold on the timing of the gradient impulses is not taken into account. The dB/dt model is thus only a worst-case estimate, which, in many cases, allows the capability of modern gradient systems to be used only within certain limits.

Another known approach to stimulation monitoring is known as the "Irnich model". This method describes the stimulation threshold value as a factor of the duration $t_E$ of the external influence. The duration $t_E$ is the time in which the gradient changes in one direction; i.e., dB/dt is permanently >0, or <0. A more detailed explanation can be found in the article "Electrostimulaticn by time-varying magnetic fields" (W. Irnich, MAGMA; 1994; 2:43–9. Represented as the dB/dt value, the threshold is therein proportional to $(1+t_{chron}/t_E)$, i.e. is hyperbolically dependent on the duration of effect $t_E$. The chronaxie time $t_{chron}$ is a physiologically defined characteristic time.

The experimental results in different studies can be described well with the Irnich model. The results of these studies are discussed in the article "Magnetostimulation in MRI" (W. Irnich, F. Schmitt; MRM; 1995;33:619–23), and in the article "Threshold and Pain Strength-Duration Curves for MRI Gradient Fields" (J. D. Bourland; Proc. SMRM; 1997:1974). Nevertheless, it is possible to apply the Irnich model with a fixed set of parameters only to one characteristic gradient pulse shape, given which the alteration of the duration of $t_E$ is performed globally, i.e. for each individual pulse in a like manner. A discrepancy thus arises when trapezoidal pulses with a corresponding duration of effect $t_E$ are used instead of sinusoidal pulses. The method which is based on the Irnich model is also not usable if mere single pulses within a long pulse train generate particularly high dB/dt values (e.g. blip pulses). In addition, the Irnich model does not take into account the dependency of the stimulation threshold on the number of individual pulses in a pulse train. In this respect, one can refer to FIG. 4 of the article "Physiological Effects of Fast Oscillating Magnetic Field Gradients" (Th. F. Budinger, *J. Computer Assisted Tomography*, 1991;15(6):909–14. The dependency on what are known as plateau times in sinusoidal excitations is not taken into account, either, such as can be seen in FIG. 7 of the essay "Peripheral Nerve Stimulation by Time-Varying Magnetic Fields"; *J. Computer Assisted Tomography* (4):532–38.

SUMMARY OF THE INVENTION

An object of the present invention is to provide a method which avoids electrical stimulations in an examination subject who is exposed to rapidly switched gradient fields of high amplitude can be avoided.

This object is inventively achieved in a method wherein at least one gradient signal $G(t)$ determined that is defined by the time characteristic of the gradient pulses, at least one first filtered gradient signal $G_{F1}(t)$ is formed by filtering the gradient signal $G(t)$ with a first filtering function $f_{F1}(t)$, from the first filtered gradient signal $G_{F1}(t)$, a stimulation signal $Stim(t)$ is formed which describes the stimulation of the examination subject, and the stimulation signal $Stim(t)$ is compared to a predetermineable stimulation threshold value $Stim_{lim}$, and if the threshold value $Stim_{lim}$ is exceeded, a signal is emitted.

The above object is also achieved in an apparatus having at least two parallel circuit paths, a first of which is a series circuit formed by it least one low pass filter followed by a rectifier and a second of which is a series circuit formed by a rectifier followed by at least one low pass filter, an input stage whose input signal is the gradient signal $G(t)$ and whose output signal is fed to both the paths as a path input signal, and an adder which adds the output signals of the two paths, forming at least one stimulation signal $Stim(t)$ with a predetermineable weighting, which signal describes the stimulation of the examination subject.

The inventive method can be applied to one, two or all three gradient coils, which represent physical gradient axes, respectively. The number of gradient coils from the total of three to which this method is applied ultimately depends on the particular MR device, on the desired pickups and on the permissible stimulation threshold values $Stim_{lim}$.

If all three gradient coils are switched simultaneously (e.g. given tilted or rotated slices), then it can be checked for each gradient axis separately whether or not a stimulation is produced. This may not be sufficient, however, since a stimulation can be triggered, for example, by the simultaneous influence of all three gradient coils, although the stimulation threshold has not yet been exceeded for each individual coil. In an embodiment of the invention, a check as to whether stimulations can be triggered by the simultaneous influence of all three gradient coils can be realized easily, such as by combining the three ratios $Stim_x(t)/Stim_{lim,x}$, $Stim_y(t)/Stim_{lim,y}$, and $Stim_z(t)/Stim_{lim,z}$.

In a further version of this check, it can be checked whether the following condition is satisfied for each time t (the additional indices relate to the observed respective physical gradient axes x,y,z):

$$[(Stim_x(t)/Stim_{lim,x})^2+(Stim_y(t)/Stim_{lim,y})^2+(Stim_z(t)/Stim_{lim,z})^2]^{1/2} < Stim_{factor}$$

wherein $Stim_{factor}$ designates the stimulation factor which describes the stimulation caused by the influence of all three gradient coils (gradient axes). For the stimulation factor $Stim_{factor}$, the following inequality applies: $Stim_{factor} \leq 1$.

When the aforementioned condition is satisfied, then stimulations do not arise. When this condition is not satisfied, i.e. when the sum on the left side of the inequality is greater than the stimulation factor $Stim_{factor}$, then stimulations can be expected. The inclusion of the stimulation factor $Stim_{factor}$ permits a greater flexibility in the adaptation of the inventive method to the device-specific data, which can be acquired experimentally.

A further embodiment of the device for practicing the inventive method takes into account that the simultaneous influence of at least two gradient fields can trigger a stimulation, even though the stimulation threshold for each individual gradient field has not been exceeded, and that the orthogonality of the gradient fields usually no longer exists outside the examination region. To this end, adders with predetermineable weighting add at least two stimulation signals of two gradient coils and/or at least two squared stimulation signals of two gradient coils and/or at least one stimulation signal of a gradient coil and the same signal in squared form, in order to compare the summed signals to appertaining predetermineable reference levels in a comparator unit.

In the inventive method according to Claim 1, it is sufficient to observe the gradient signals $G(t)$ without having to know their mathematical structure, which can be derived from the time characteristic and the amplitude of the gradient impulse.

The gradient signals $G(t)$ are easy to measure, since they correspond (up to a scaling factor) to the current through the related gradient coil.

In a further embodiment of the inventive method existing voltage signals of the gradient control and amplifier unit of an MR device are used as gradient signals $G(t)$. The current real value signals, or current target value signals and voltage signals, which are directly proportional to the first time derivative of a gradient coil current, are suitable for this. Given the use of current real value signals, an error of the gradient control and amplifier unit can also be monitored with the inventive device. The advantage of using current target value signals is that the attainment of stimulation thresholds in an online monitoring is recognized a few microseconds earlier than with current real value signals. Given the use of a voltage signal which is directly proportional to the first time derivative of a gradient coil current, the differentiation that is necessary for the current real value signals and target value signals not needed. This voltage signal is usually available as an output voltage of the gradient control and amplifier unit.

By filtering the differentiated gradient signal $G_{diff}$ with a first filtering function $f_{F1}(t)$ and with a second filtering function $f_{F2}(t)$, in another embodiment of the invention, the stimulations which are induced by an external electrical field and the further conduction of these stimulations in the nervous system are approximately modeled. The first filtering function $f_{F1}(t)$ describes the excitement of the action potential on the presynaptic side, which causes chemical messenger substances to be diffused out. These messenger substances are absorbed on the postsynaptic side, i.e., in a nerve cell downstream, where they trigger a further action potential. The excitation of the action potential on the postsynaptic side is described by the second filtering function $f_{F2}(t)$. Since the original polarity of the excitation is no longer contained in the action potential on the postsynaptic side, in a further embodiment of the invention, the result of the first filtering function $f_{F1}(t)$ is rectified to Abs ($f_{F1}(t)$), and only the rectified portion of the differentiated gradient signal $G_{diff}$ is processed by the second filtering function $f_{F2}(t)$.

Although a knowledge of the mathematical structure of the gradient signals is not necessary in the inventive method, the inventive method offers a better approximation with reference to stimulation prediction than previously known methods. This results from the fact that not only are the dependencies that are described by the Irnich model taken into account, but also the shape of the gradient impulse (e.g. trapezoidal, sinusoidal, blip impulse), the number of individual impulses generated by the NMR device, and the included plateau times are taken into account, but without observing their mathematical structure. Furthermore, the degree of accuracy can be arbitrarily improved by the use of additional filtering functions.

In an embodiment of the device for practicing the inventive method, a refined simulation of the processes in the relaying of stimulations in the nervous system is achieved. To this end, the low passing is carried out in the first path by a parallel arrangement of two low pass filters and an adder which is connected downstream, which adds the output signals of the two low pass filters with a specifiable weighting. In the second path, at least one additional low pass filter is connected to the originally-cited low pass filter in parallel fashion, the output signal of the additional filter also being added by the adder with a specifiable weighting.

The inventive method can be realized as a hardware or software solution, or as a mixed hardware-software solution.

Both an online monitoring and a look-ahead monitoring of the MR device are possible with the inventive method. A combination of both types of monitoring is also possible within the framework of the invention. In this context, online monitoring means monitoring during imaging. In an embodiment of the invention the measuring sequence is immediately aborted given attainment of the stimulation threshold $Stim_{lim}$. In online monitoring, an erroneous behavior of the gradient amplifier can also be monitored by means of appropriate additional measures. Look-ahead monitoring means monitoring prior to the beginning of the imaging measuring sequence. Furthermore, a wide variety of imaging measuring sequences can be simulated with the inventive method. In a look-ahead monitoring and in a measuring sequence simulation, the aborting of the measuring sequence as described above is not necessary, or at least is not desirable.

In another embodiment of the inventive method the filtering of the differentiated gradient signal $G_{diff}$ is described by a convolution:

$$G_{diff}(t) \otimes \frac{1}{\tau} e^{-\frac{t}{\tau}} = \frac{1}{\tau} \int_{-\infty}^{+\infty} G_{diff}(t_1) \cdot e^{-\frac{(t-t_1)}{\tau}} dt_1,$$

the filter functions $f_{F1}(t)$ and $f_{F2}(t)$ being realized by an exponential function with a specifiable time constant $\tau$.

For the case $\tau = \tau_1$, a first e-function (filtering function $f_{F1}(t)$) results, and for the case $\tau = \tau_2$, a second e-function (filtering function $f_{F2}(t)$) results, with which the differentiated gradient signal $G_{diff}$ is respectively physically filtered, or mathematically convolved.

In another embodiment of the Invention the stimulation threshold value $Stim_{lim}$ can also be specified for each imaging, depending on the patient. For the patient-dependent prescription of the stimulation threshold value $Stim_{lim}$, it is necessary to obtain the patient's individual stimulation threshold by a suitable measurement at the patient, e.g. by an electrical conductivity measurement. Then the stimulation threshold value $Stim_{lim}$ need only be scaled accordingly.

In a further version of the inventive method, the function of the inventive filtering method can be changed to a pure dB/dt monitoring. By the selection of a sufficiently large value for the limit frequency of the first filtering function $f_{F1}(t)$, its filtering effect is nearly eliminated. By the selection of a sufficiently small value for the second weighting factor $a_2$ (the weighting factor for the second filtered gradient signal $G_{F2}(t)$), the filtering result of the second filtering function $f_{F2}(t)$ is effectively ignored.

The inventive method allows for developments which take into account further parameters besides those discussed above. Among these further parameter are the orientation of the patient in the patient tube of the magnet (e.g. lying on the back or side, head or feet first) or his/her position in the z-direction (i.e. the body part onto which the positioning occurs), for example.

DESCRIPTION OF THE PREFERRED EMBODIMENTS

Figure 1:
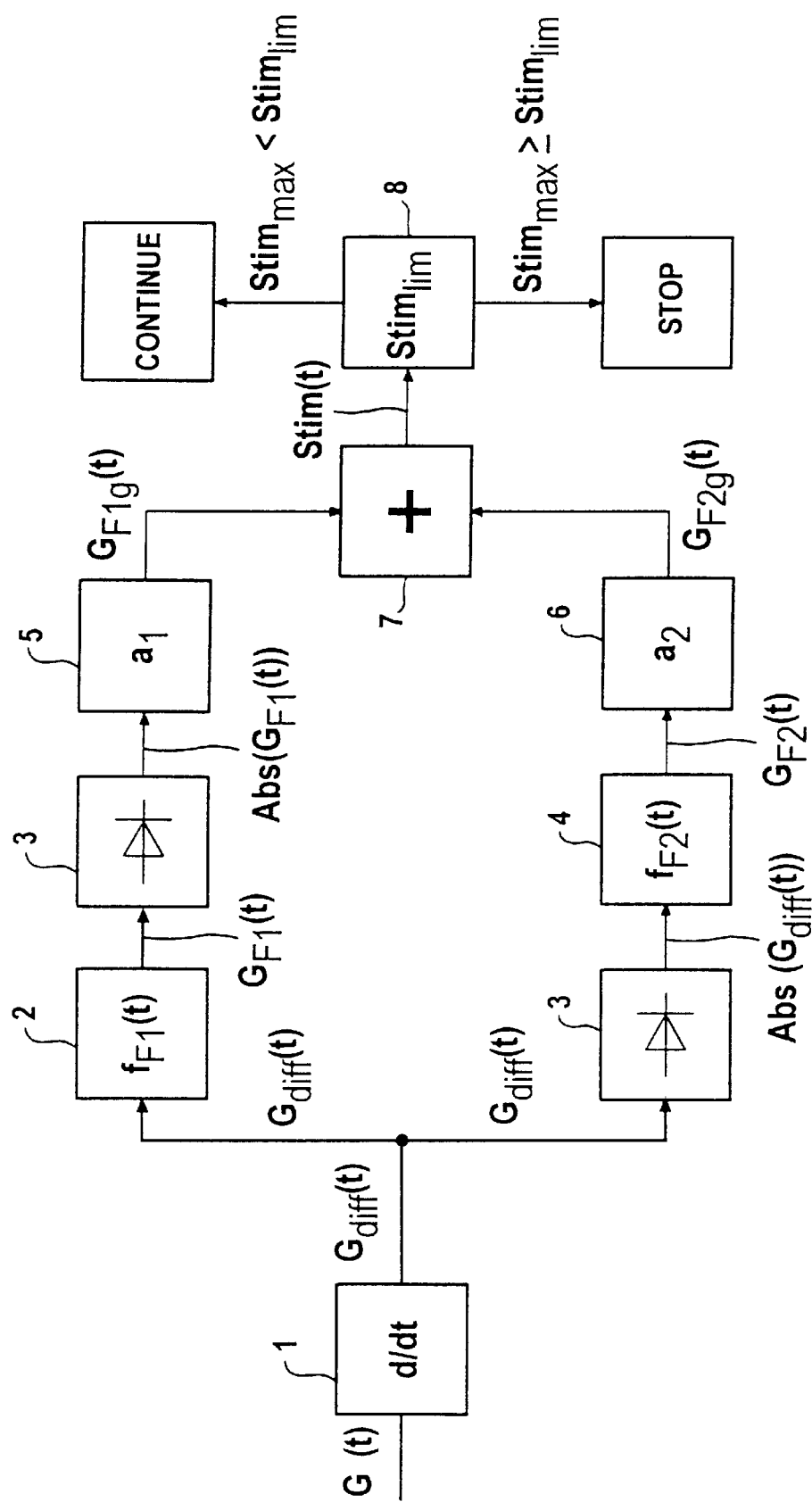
FIG. 1 is a flow chart of an embodiment of the inventive method.
Figure 2:
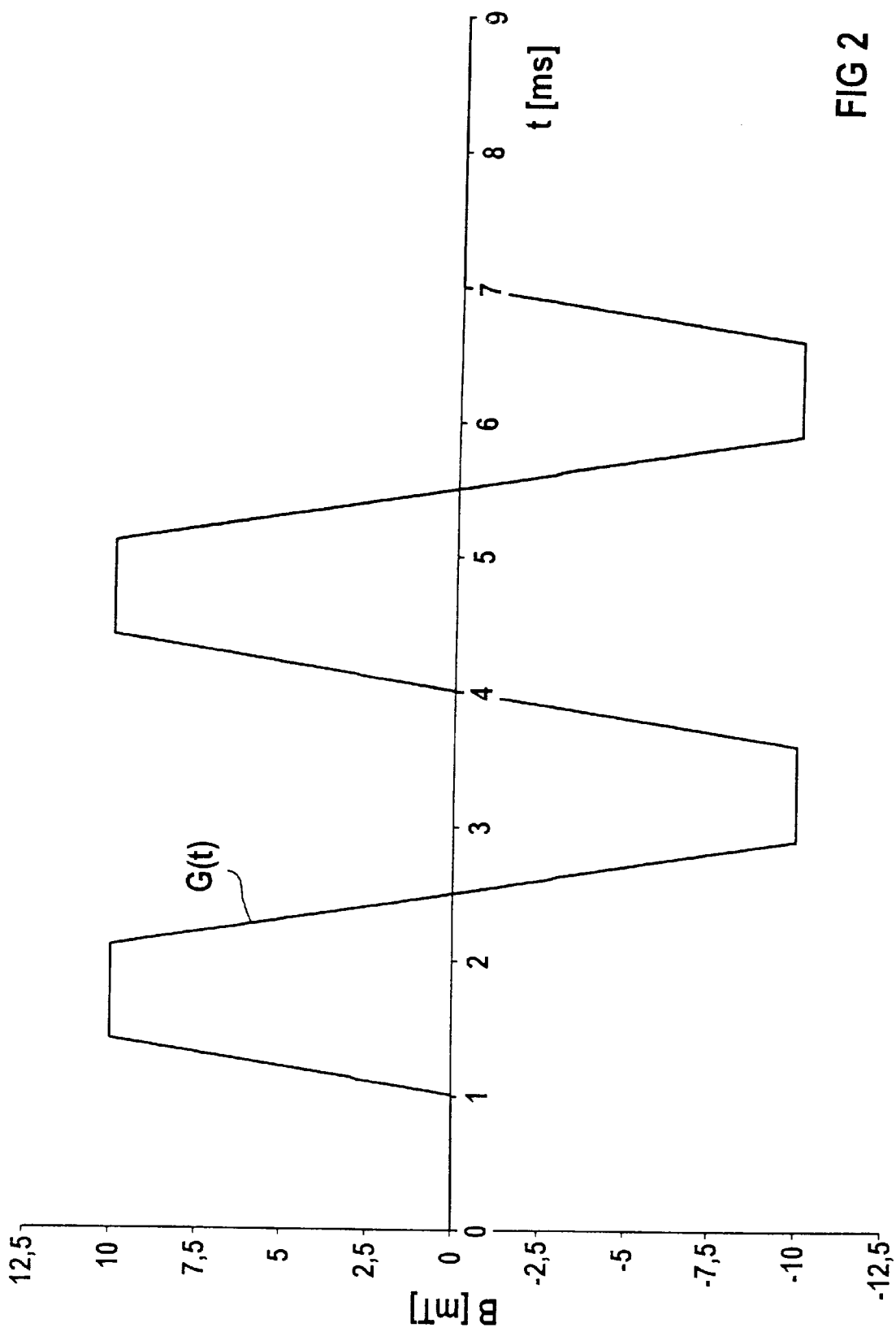
FIGS. 2 through 7 respectively show the time characteristics of signals which are measured in an embodiment of the inventive method, and of signals formed according to this method.

The flow chart according to FIG. 1 begins with a differentiation stage 1 to which a gradient signal G(t) is fed. The gradient signal G(t) has the time characteristic which is illustrated in FIG. 2. A preferred embodiment of the inventive method is detailed below using a trapezoidal gradient signal (trapezoidal pulse) with the amplitude $B_0 = 10$ mT.

The dimension of the gradient impulse and thus of the gradient signal G(t) are mT/m. The spatial dependency of the magnetic field which is generated by the gradient coil is not considered more closely below. Rather, with G=G(t), the gradient field which is defined by the gradient coil is observed at a fixed point in space. The scaling factor in the transition from the gradient signal to the magnetic field is determined by the gradient coil that is used and the point in space that is observed.

Figure 3:
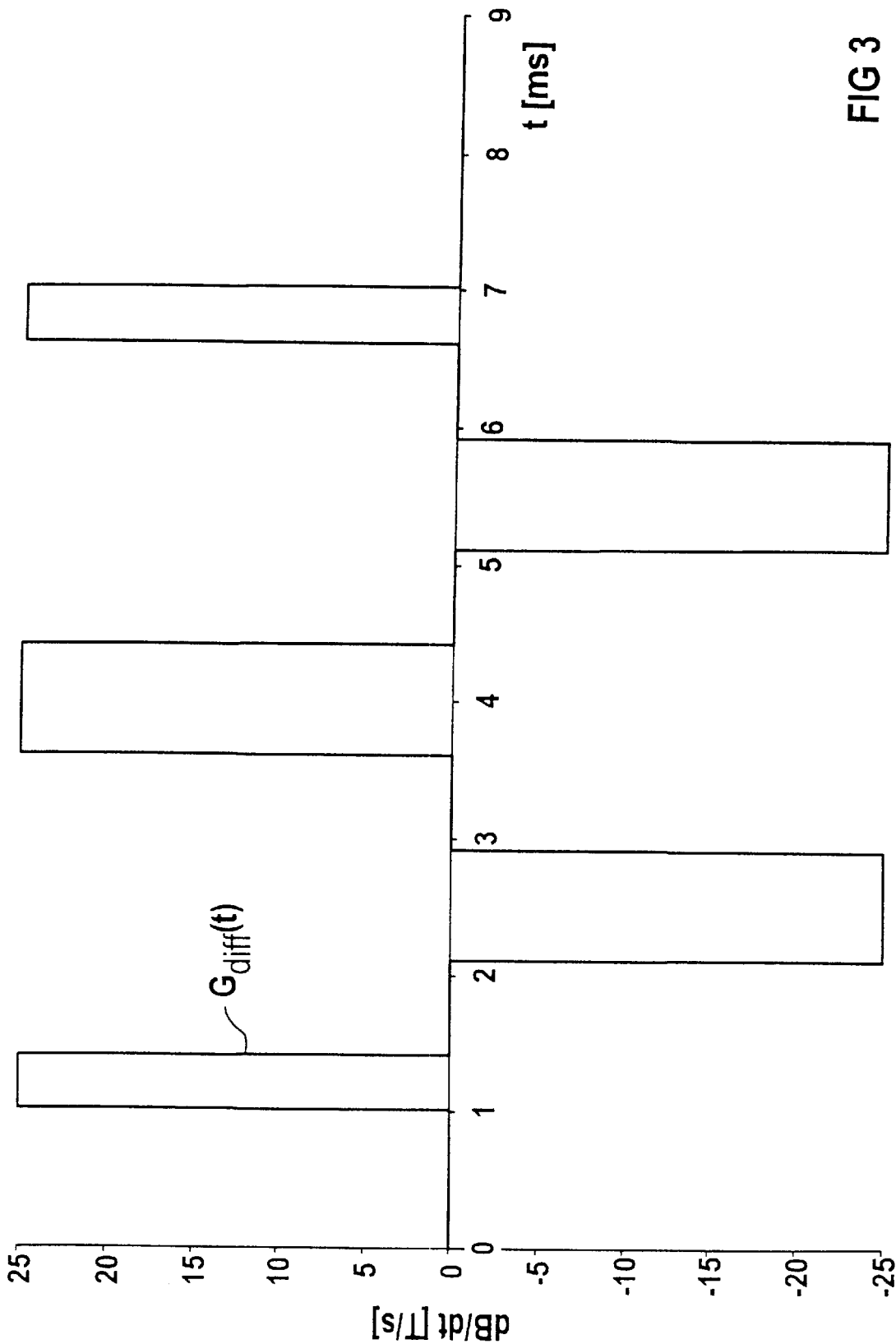

In the differentiation stage 1, a differentiated gradient signal $G_{diff}(t)$ is formed from the gradient signal G(t) by a first time derivative d/dt, the time characteristic of this differentiated gradient signal being illustrated in FIG. 3.

The differentiated gradient signal $G_{diff}(t)$ is sent to a first low pass filter stage 2 and a second low pass filter stage 4. In the illustrated exemplifying embodiment, the two low pass filter stages 2 and 4 are arranged parallel to one another and are connected downstream from the differentiation stage 1. A rectifier stage 3 is present downstream of the first low pass filter stage 2, and a rectifier stage 3 is present upstream of the second low pass filter stage 4, by means of which only the rectified portion of the differentiated gradient signal $G_{diff}(t)$ is fed to the second low pass filter stage 4. Thus, only the absolute value of the differentiated gradient signal $G_{diff}(t)$ is available for further signal processing.

In the first low pass filter stage 2, the differentiated gradient signal $G_{diff}(t)$ is filtered with a first filtering function $f_{F1}(t)$. In the second low pass filter stage 4, the absolute value of the differentiated gradient signal $G_{diff}(t)$ is filtered with a second filtering function $f_{F2}(t)$.

In the described development of the inventive method, the two filtering functions $f_{F1}(t)$ and $f_{F2}(t)$ are defined as follows:

$$f_{F1}(t) = \frac{1}{\tau_1} e^{-\frac{t}{\tau_1}} \text{ and } f_{F2}(t) = \frac{1}{\tau_2} e^{-\frac{t}{\tau_2}},$$

wherein $\tau_1$ and $\tau_2$ are selected time constants.

The stimulations caused by an external electrical field and the relay (transmission) thereof in the nervous system are approximately described by the filtering of the differentiated gradient signal $G_{diff}(t)$ with a first filtering function $f_{F1}(t)$ and by filtering of its rectified portion $Abs(G_{diff}(t))$ with a second filtering function $f_{F2}(t)$. The first filtering function $f_{F1}(t)$ herein describes the excitation of the action potential on the presynaptic side, which causes chemical messenger substances to be diffused out. These messenger substances are absorbed on the postsynaptic side, i.e. in nerve cells downstream, where they trigger a further action potential. The excitation of the action potential at the postsynaptic side is described by the filtering function $f_{F2}(t)$. Since the original polarity of the excitation is no longer contained in the action potential at the postsynaptic side, only the rectified portion of the differentiated gradient signal $G_{diff}(t)$, which is designated $Abs(G_{diff}(t))$, is processed in the second low pass filter stage 4.

Thus, the filtering of the differentiated gradient signal $G_{diff}(t)$ in the first low pass filter stage 2 simulates the presynaptic behavior. Analogously, the post-synaptic behavior is mapped as a model in the second low pass filter stage 4.

Figure 4:
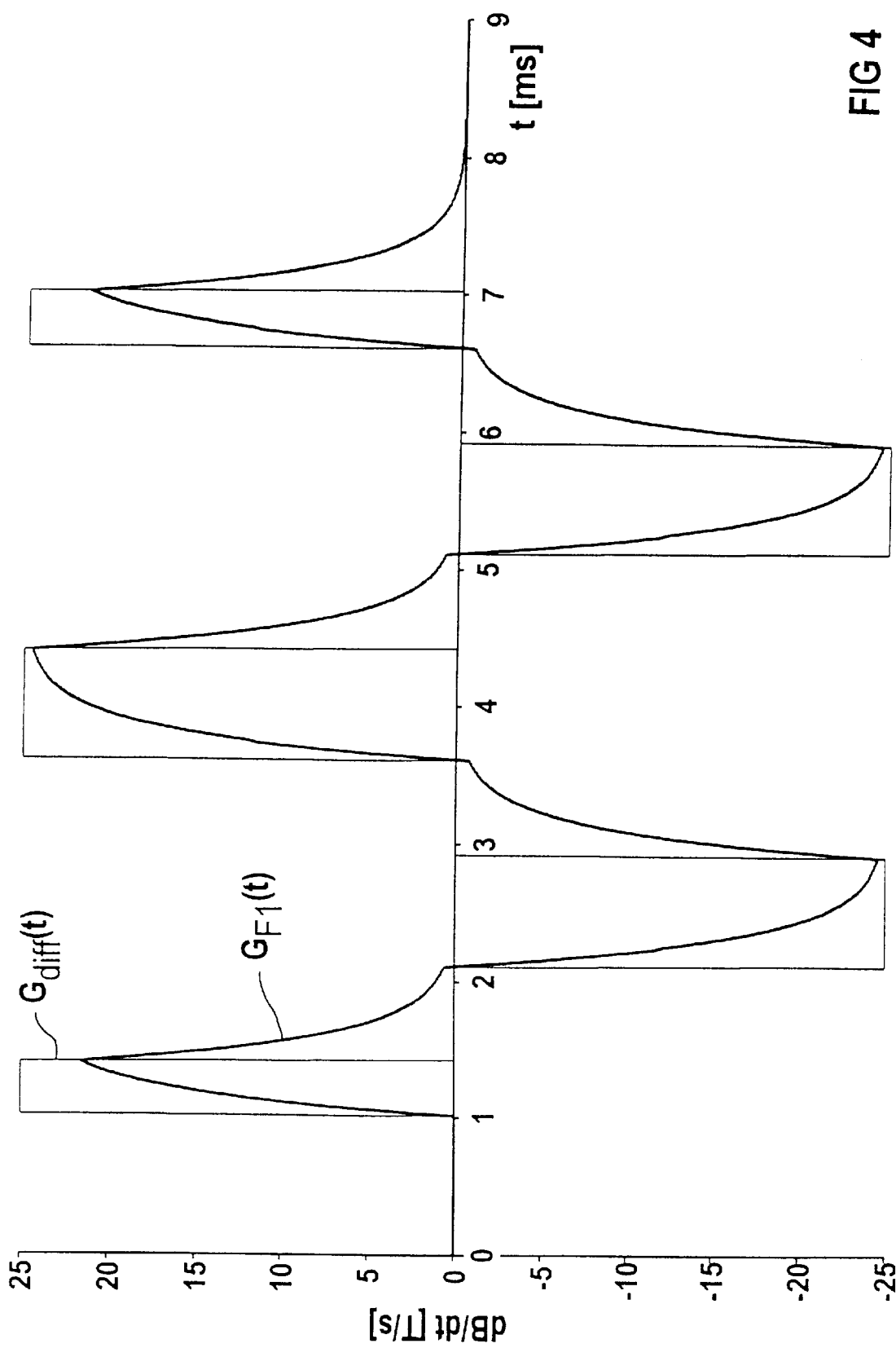

The time characteristic of the first filtered gradient signal $$G_{F1}(t) = G_{diff}(t) \otimes \frac{1}{\tau_1} e^{-\frac{t}{\tau_1}}$$

is illustrated in FIG. 4, with $\tau_1$=0.2 ms selected for the first time constant. For comparison, the differentiated gradient signal $G_{diff}(t)$ is also included in FIG. 4.

Figure 5:
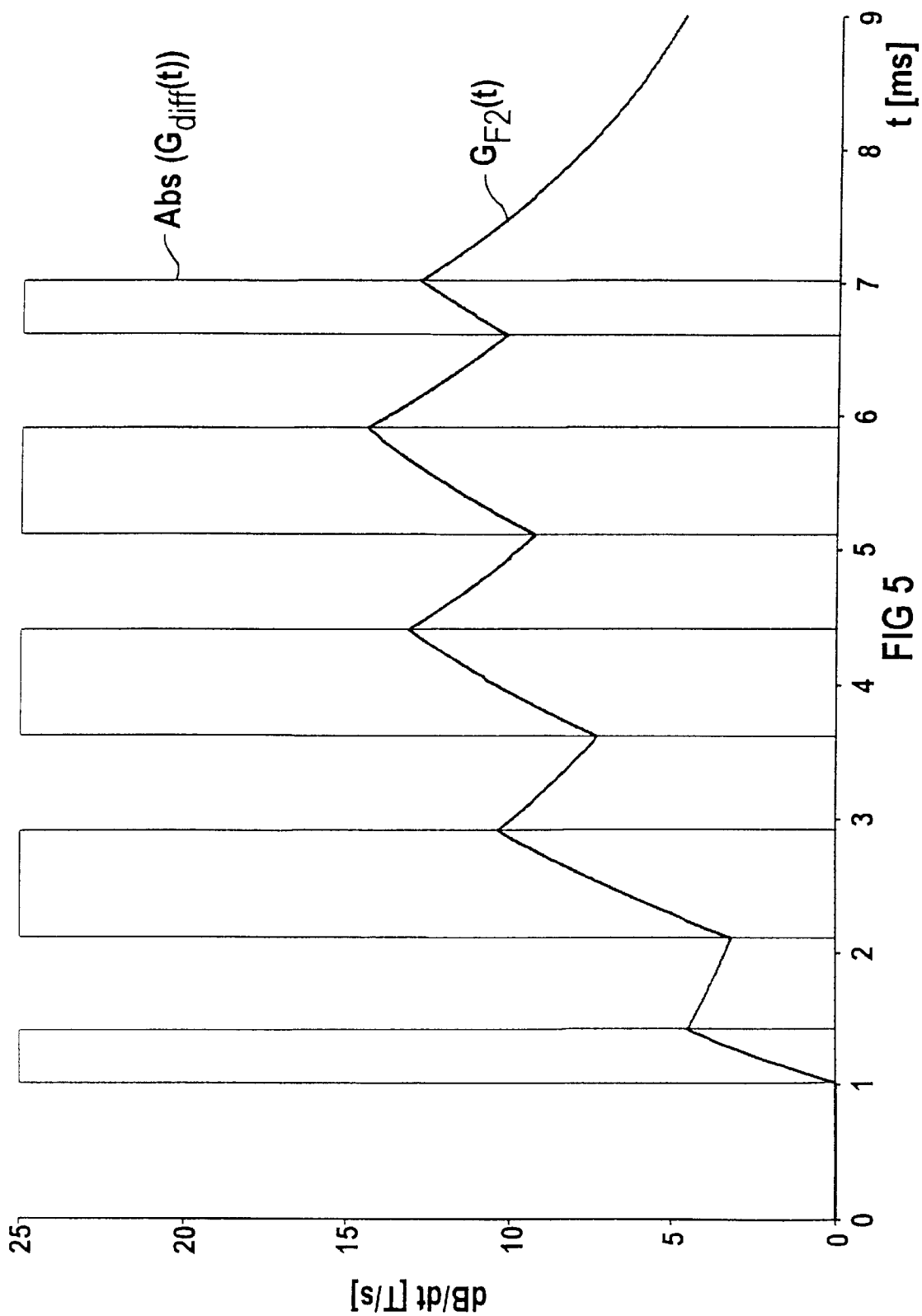

FIG. 5 depicts the time characteristic of the second filtered gradient signal $$G_{F2}(t) = Abs(G_{diff}(t)) \otimes \frac{1}{\tau_2} e^{-\frac{t}{\tau_2}}$$

whereby the second time constant $\tau_2$=2.0 ms has been selected. For comparison, the absolute value of the differentiated gradient signal $G_{diff}(t)$, designated $Abs(G_{diff}(t))$, is also included in FIG. 5.

The first filtered gradient signal $G_{F1}(t)$ and the second filtered gradient signal $G_{F2}(t)$ each undergoes a weighting in a further step. In the exemplary embodiment, this occurs by the multiplication of the rectified first filtered gradient signal $Abs(G_{F1}(t))$ by a specifiable first weighting factor $a_1$, and the multiplication of the second filtered gradient signal $G_{F2}(t)$ by a specifiable second weighting factor $a_2$. The first filtered gradient signal $G_{F1}(t)$ is fed for this purpose to a first multiplier stage 5, and the second filtered gradient signal $G_{F2}(t)$ is fed to a second multiplier stage 6. For the weighting factors $a_1$ and $a_2$ the following equation applies: $a_1+a_2=1$. In the exemplary embodiment, $a_1$=0.6 and $a_2$=0.4.

In the first multiplication stage 5, a first weighted and filtered gradient signal $G_{F1g}(t)=a_1 \cdot Abs(G_{F1}(t))$ is thus obtained.

Analogously, in the second multiplication stage 6, a second weighted and filtered gradient signal $G_{F2g}(t)=a_2 \cdot G_{F2}(t)$ is obtained.

The two weighted and filtered gradient signals $G_{F1g}(t)$ and $G_{F2g}(t)$ are combined by a freely selectable logic operator into a stimulation signal Stim(t). In the present exemplary embodiment, the combining occurs by addition of the two weighted and filtered gradient signals $G_{F1g}(t)$ and $G_{F2g}(t)$. The two weighted and filtered gradient signals $G_{F1g}(t)$ and $G_{F2g}(t)$ thus are fed to an adder stage 7 for this purpose.

The resultant stimulation signal Stim(t) is thus as Stim(t)=$G_{F1g}(t)+G_{F2g}(t)$.

Figure 6:
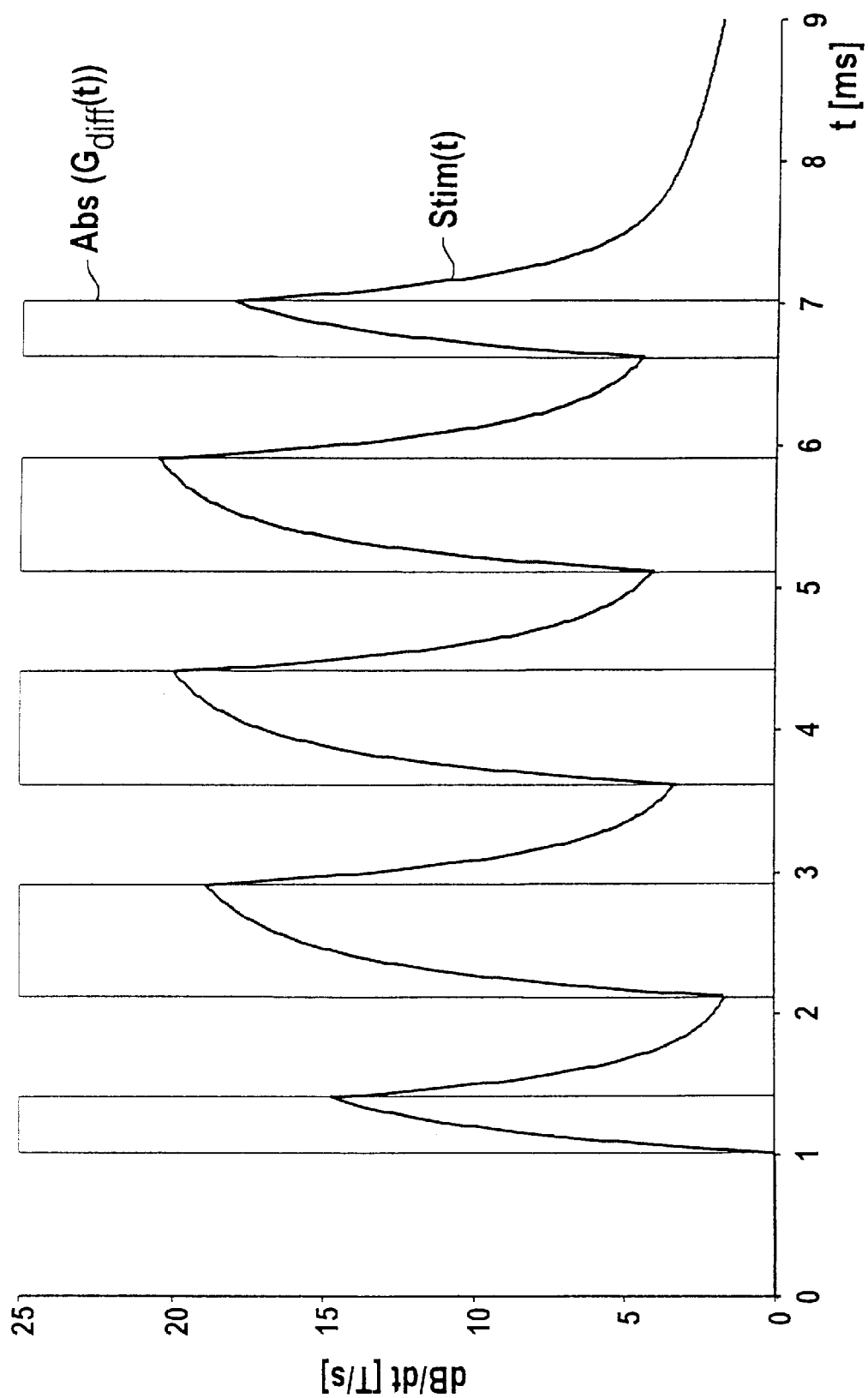

FIG. 6 illustrates the characteristic of the stimulation signal Stim(t). For comparison, the absolute value of the differentiated gradient signal $G_{diff}(t)$, designated $Abs(G_{diff}(t))$, is included in FIG. 6.

The stimulation signal Stim(t) which is so obtained is fed to a comparator stage 8.

In the comparator stage 8, the stimulation signal Stim(t) is compared to a specifiable stimulation threshold $Stim_{lim}$. If the detected stimulation signal Stim(t) attains or exceeds a characteristic limit value $Stim_{lim}$ for the gradient coil, then this is an indicator of the occurrence of stimulations. In the given exemplary embodiment, the maximum stimulation value $Stim_{max}$ of the stimulation signal Stim(t) is determined and is compared with the specifiable stimulation threshold value $Stim_{lim}$. If the maximum stimulation value $Stim_{max}$ is greater than the stimulation threshold value $Stim_{lim}$, then stimulations are expected to occur; otherwise, they are not.

If no stimulations are to be expected, then the imaging measuring sequence is continued (as indicated by the CONTINUE block). If so desired, the maximal stimulation value $Stim_{max}$ can be continuously logged.

In the exemplary embodiment, which involves online monitoring, if the stimulation threshold value $Stim_{lim}$ is exceeded, the imaging is at least temporarily interrupted (as indicated by the STOP block). The ratio $Stim_{lim}/Stim_{max}$, which is obtained from the specifiable stimulation threshold value $Stim_{lim}$ and the maximum stimulation value $Stim_{max}$ (and which is <1), is used directly as a scaling factor for the amplitude of the gradient signal G(t). Stimulations then no longer arise in a renewal imaging sequence.

Figure 7:
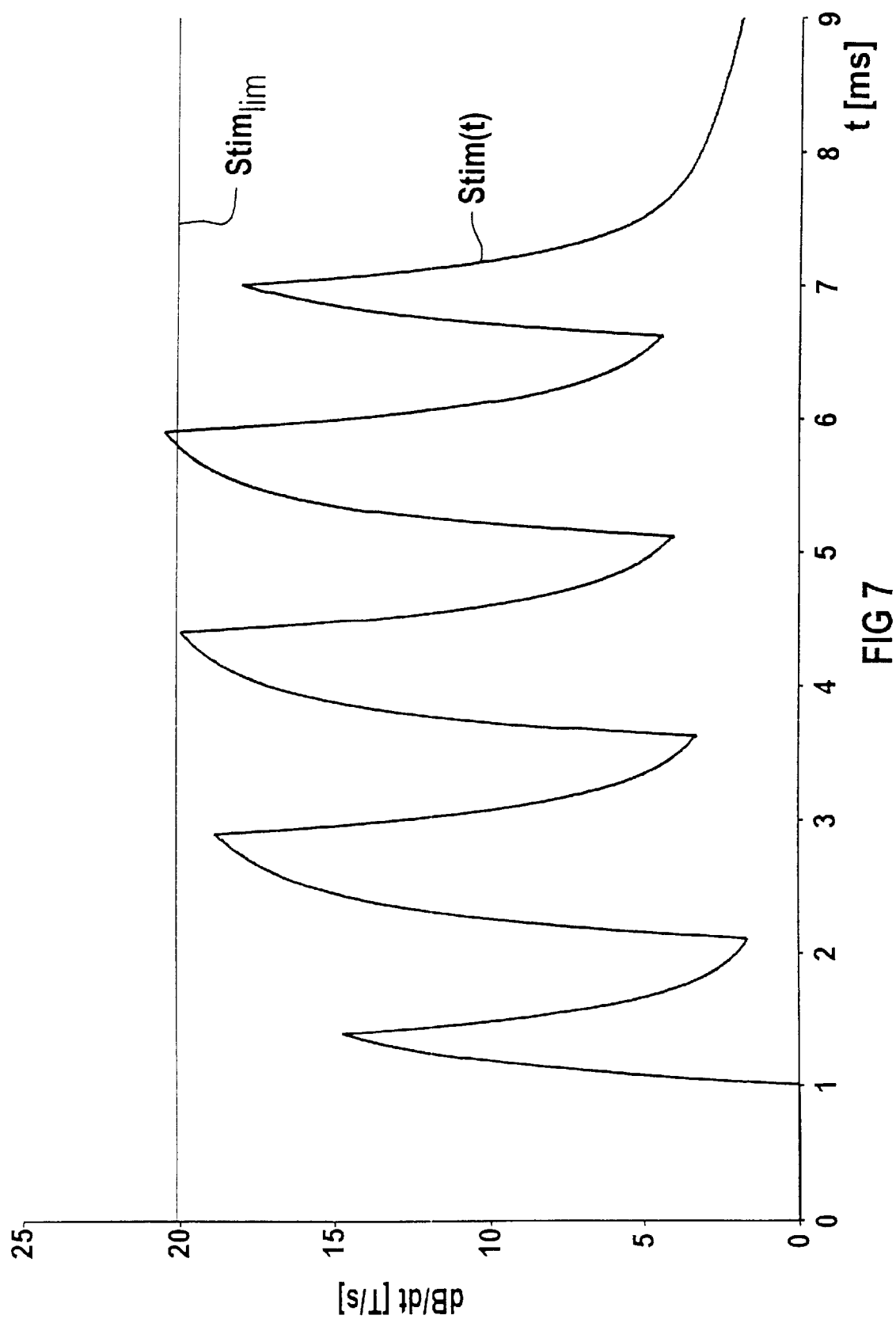

In the characteristic of the stimulation signal Stim(t) illustrated in FIG. 7, $Stim_{lim}$=20.1 T/s is selected for the stimulation threshold value.

As can be seen in FIG. 7, in this example a stimulation would be triggered by the trailing edge of the third gradient signal after some 6 ms, although the arising nominal dB/dt values are constant for all individual gradient pulses.

The filtering of the differentiated gradient signal $G_{diff}(t)$ which is to be performed in the inventive method can be easily calculated mathematically as a filtering function employing an exponential function.

Below, $G_n=G_{diff}(n·\Delta t)$ designates the differentiated gradient signal at a time $(n·\Delta t)$, and $G_{Fn}=G_F(n·\Delta t)$ designates the filtered gradient signals $G_{F1}(t)$ and $G_{F2}(t)$ at a time $(n·\Delta t)$. $\Delta t$ represents the sampling interval.

With $c_1=e^{-\Delta t/\tau}$ and $c_2=1-c_1$, the filtered gradient signal $G_{Fn}$ can then be calculated iteratively from the differentiated gradient signal $G_n$ (input signal of the low pass filter stage 2 or 4 and the already calculated values of $G_{Fn}$, according to the following relation:

$$G_{Fn}=c_1·G_{Fn-1}+c_2·G_n.$$

Figure 8:
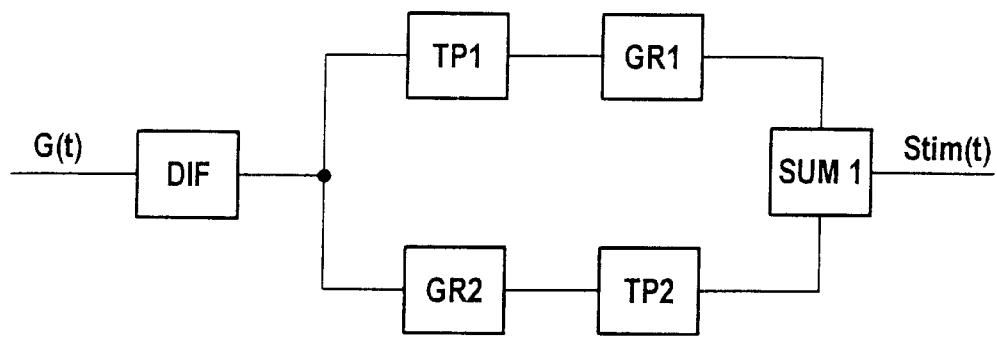
FIG. 8 is a block diagram of a first embodiment of an apparatus in accordance with the invention for conducting the inventive method.

The flow chart depicted in FIG. 1 for monitoring the stimulation thresholds is realized in an exemplary electrical circuit shown in FIG. 8. Thus, for example, convolution of the differentiated gradient signal with an e-function corresponds to the behavior of a low-pass circuit comprised of a resistor and a capacitor.

FIG. 8 depicts an exemplifying embodiment for realizing the flow chart which is depicted in FIG. 1 from the gradient signal G(t) to the stimulation signal Stim(t). The differentiator DIF, the low pass filters TP1 and TP2, the rectifiers GR1 and GR2 and the adder SUM1 are thus composed of operational amplifiers OPAMP, resistances R and capacitances C, in corresponding circuit modules according to FIG. 10 through FIG. 16. The gradient signal G(t) is a voltage signal which is directly proportional to the current in a gradient coil, which is determined by a gradient pulse sequence.

In FIG. 8, the gradient signal G(t) is fed to a differentiator DIF. The output signal of the differentiator is fed to a first low pass filter TP1, whose output signal is fed to a first rectifier GR1. The output signal of the differentiator is simultaneously fed to a second rectifier GR2, whose output signal is fed to a second low pass filter TP2. The output signals of the rectifier GR1 and of the low pass TP2 are fed to an adder SUM1, wherein they are added together, with a definable weighting, the output signal of said adder being the stimulation signal Stim(t).

Figure 10:
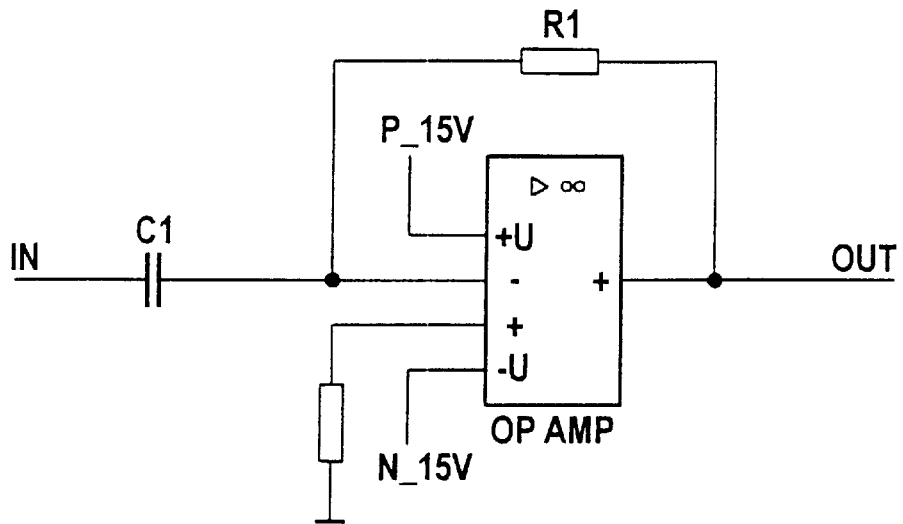
FIGS. 10 through 19 show circuit details of various electrical circuit modules for use in the apparatus embodiments shown in FIGS. 8 and 9.
Figure 11:
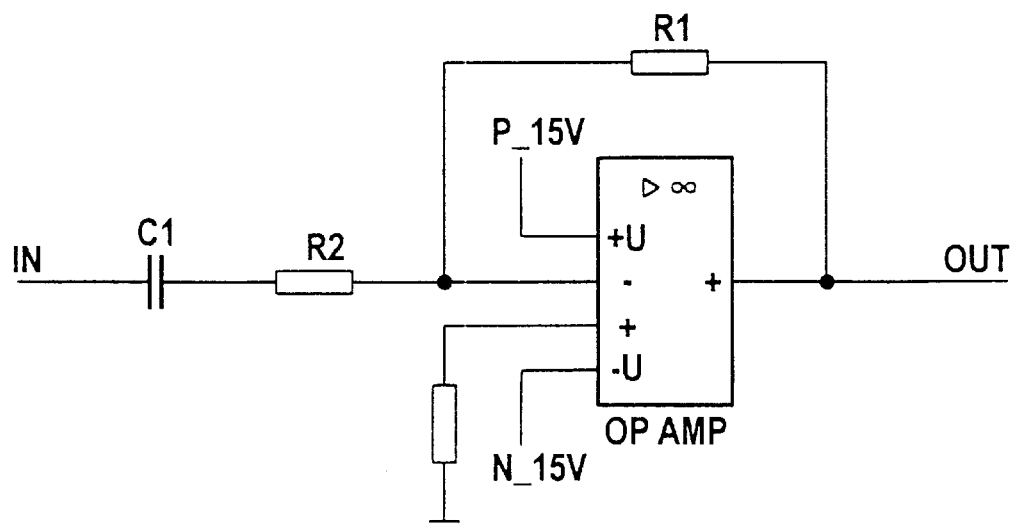

FIG. 11 depicts the differentiator DIF. The illustrated circuit is a differentiator with an integrated low pass filter with the low-pass time constant $T_{TP}$. The frequency response OUT/IN=$-j·\omega·T_{DIF}/(1+j·\omega·T_{TP})$, wherein, $T_{DIF}$=C1·R1 is the differentiator time constant, $T_{TP}$=C1·R2 is the low-pass time constant, and $\omega=2·\pi·f$ is the angular frequency, f being the frequency. In practice, the differentiator with the frequency response OUT/IN=$-j·\omega·R1·C1$, as illustrated in FIG. 10, exhibits an undesirable transient condition. This transient condition is eliminated by the integrated low pass filter. The time constant $T_{TP}$ is selected on the order of magnitude of 1 to 3 µs, so that it is rather small compared to the rise time of the gradient and is therefore negligible.

Figure 15:
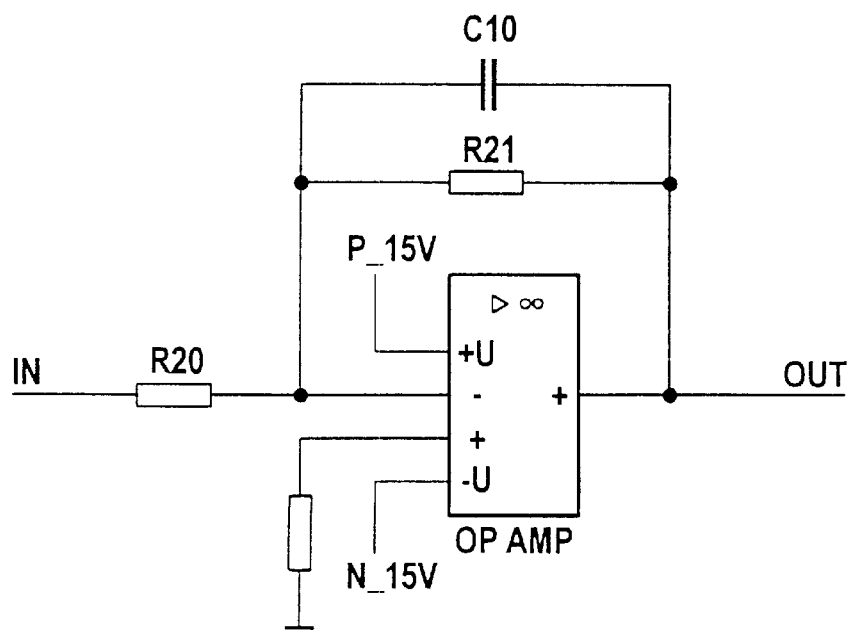
Figure 16:
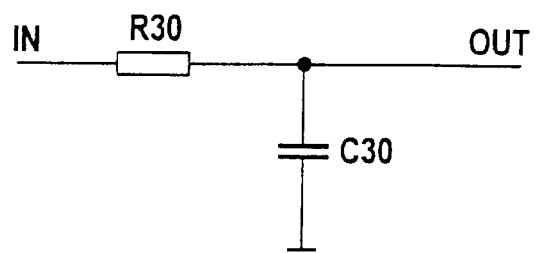

The low pass filter TP1 can be formed as a circuit with an operation amplifier OPAMP according to FIG. 15. The amplification factor is −R21/R20, the time constant is R21·C10 and the frequency response OUT/IN=−(R21/R20) ·(1/(1+j·ω·R21·C10)). A passive low pass filter according to FIG. 16 can also be used, but the impedance of the subsequent circuit should be taken into account. The passive low filter pass according to FIG. 16 has the time constant R30·C30 and the frequency response OUT/IN=1/(1+ j·ω·R30·C30). The use of a passive low pass filter conserves components although it complicates the calculation of the time constants and weighting factors.

Figure 12:
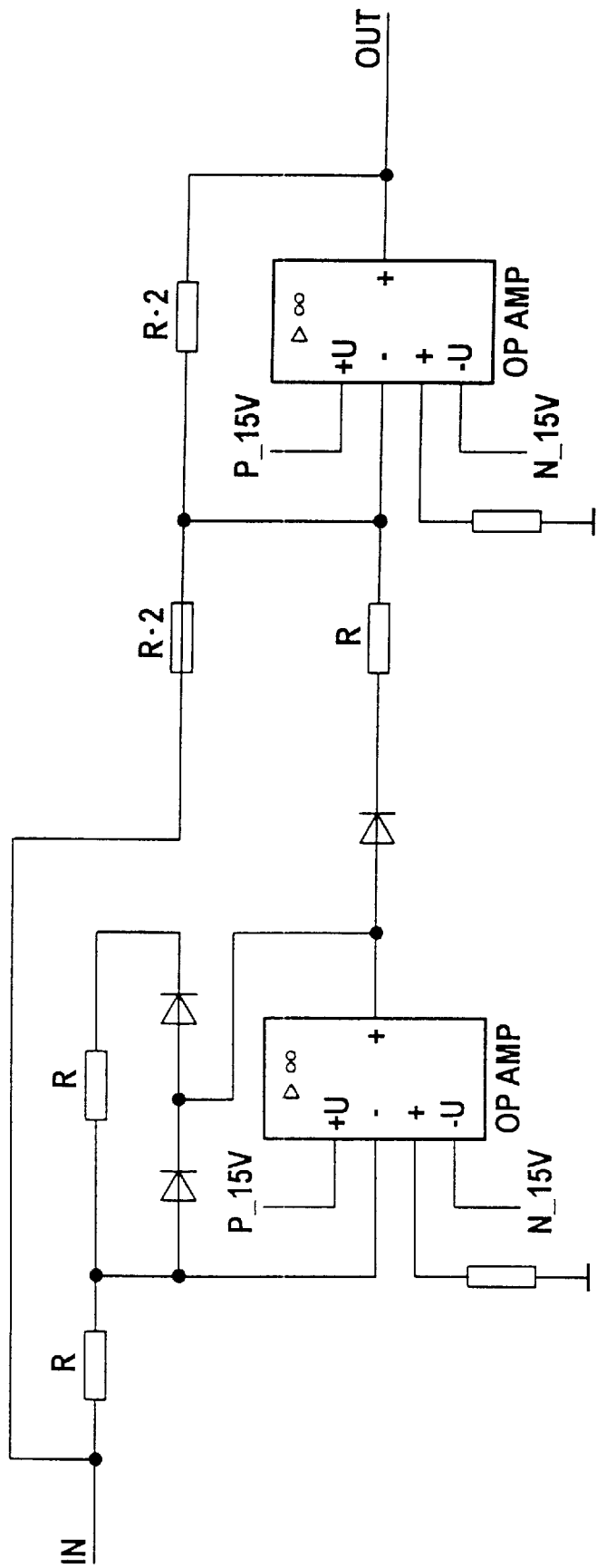
Figure 13:
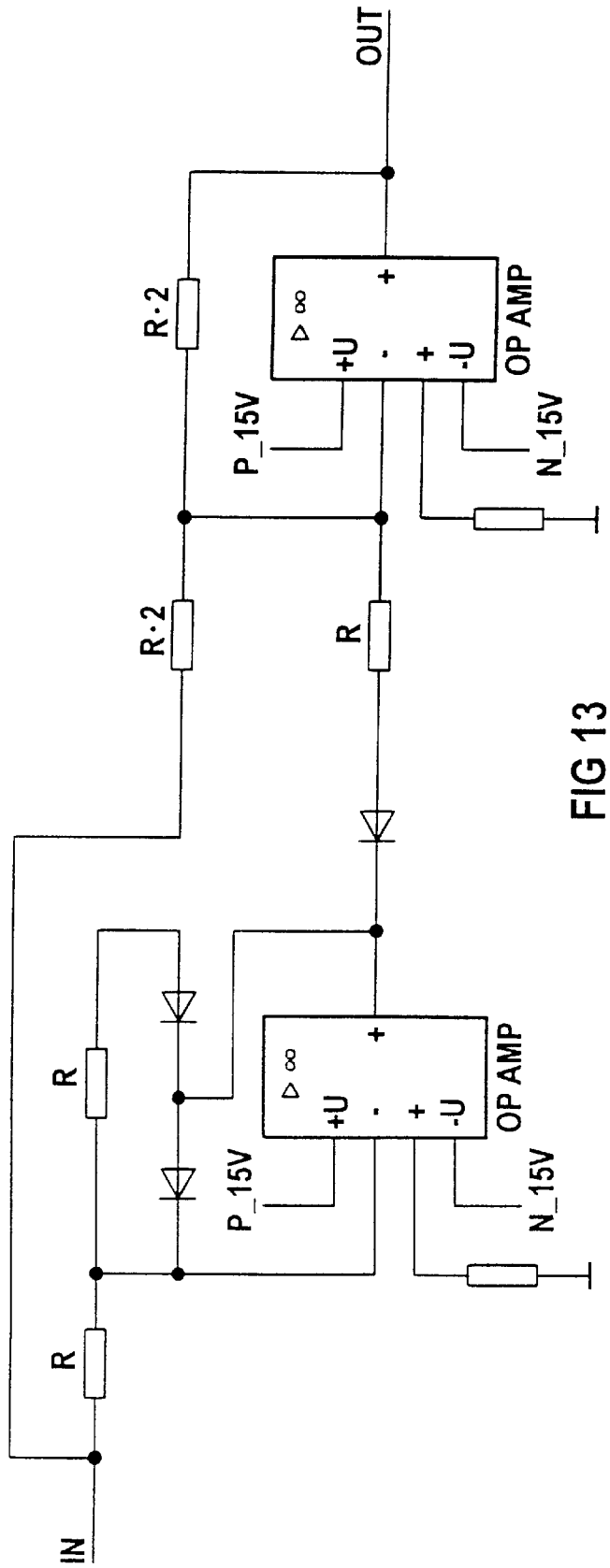

The rectifier GR1 corresponds to the circuit depicted in FIG. 12. It delivers a negative output voltage OUT independently of the sign of the input voltage IN, i.e. OUT=− Abs(IN). The rectifier GR2 corresponds to the circuit in FIG. 13 and always delivers a positive output voltage OUT, independent of the sign of the input voltage IN, i.e. OUT= Abs (IN). The dimensioning with the resistance values R and 2·R respectively illustrated in FIG. 12 and FIG. 13 effects a correspondence between the output voltage and the negative or positive value of the input voltage; i.e., there is a gain of one.

Figure 14:
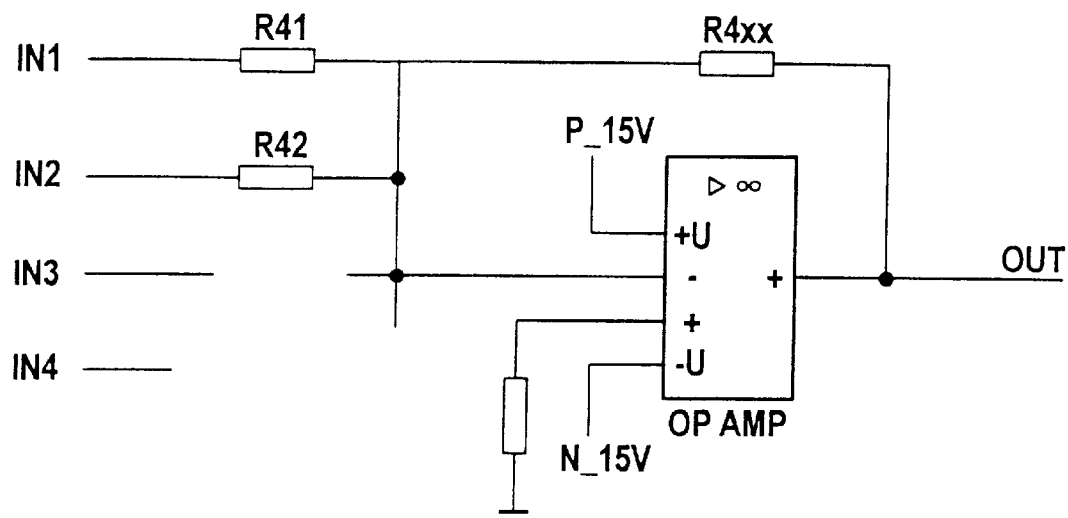

The low pass filter TP2 corresponds to the circuit according to FIG. 15. The adder SUM1 is generally illustrated in FIG. 14. The weighting of the input signals relative to one another is set by the resistors R41 and R42, and the resistor R4xx is responsible for the total gain. Given two input voltages IN1 and IN2, the following equation applies to the output voltage OUT of the adder: OUT=−(IN1·R4xx/R41+ IN2·R4xx/R24). It is guaranteed by the two different rectifiers (GR1 and GR2 that the two input voltages of the adder SUM1 have the same sign.

A good dimensioning of the circuit according to FIG. 8 is achieved when the individual signal levels are high relative to disturbing influences, but an overcontrolling of individual circuit parts is avoided. It is assumed below that the supply voltage of the operation amplifier is +/−15V.

Taking the example of the fastest possible rise time of the gradient signal of 100 µs, the output voltage of the differentiator is 10V. The time constant $T_{DIF}$=R1·C1 is thus 100 µs. If C1 is defined as 1 nF, then R1 becomes 100 kΩ. The resistance R2 is determined experimentally. It is preferably under 5 kΩ.

In order to maintain the signal level of 10V, the two resistances R21 and R20 of the low pass filters are selected so as to be equally large. If the time constant of the first low pass filter TP1 is defined as 0.2 ms and R21 is defined as 10 kΩ, then a value of 20 nF results for C10. The dimensioning of the second low pass filter TP2 with the exemplary time constant of 2 ms results in a capacitance value of 200 nF with a resistance of 10 kΩ.

Since the rectifiers GR1 and GR2 have a gain of one, the maximum level of 10 V is maintained. The adder SUM1 weights and adds the output signals OUT(GR1) and OUT (TP2) of rectifier GR1 and low pass filter TP2. If said signals are to be valued 0.6 and 0.4, for example, and if the 10V level is to be maintained, then the following dimensioning applies:

10V=−((OUT(GR1)·R4xx/R41)+OUT(TP2)·R4xx/R42)).

The output signal level of rectifier GR1 and low pass filter TP2 is −10V, resulting in R4xx/R41=0.6 and R4xx/R42=0.4. If R4xx is set at 10 kΩ, then R41=16.666 kΩ and R42=25 kΩ.

Figure 9:
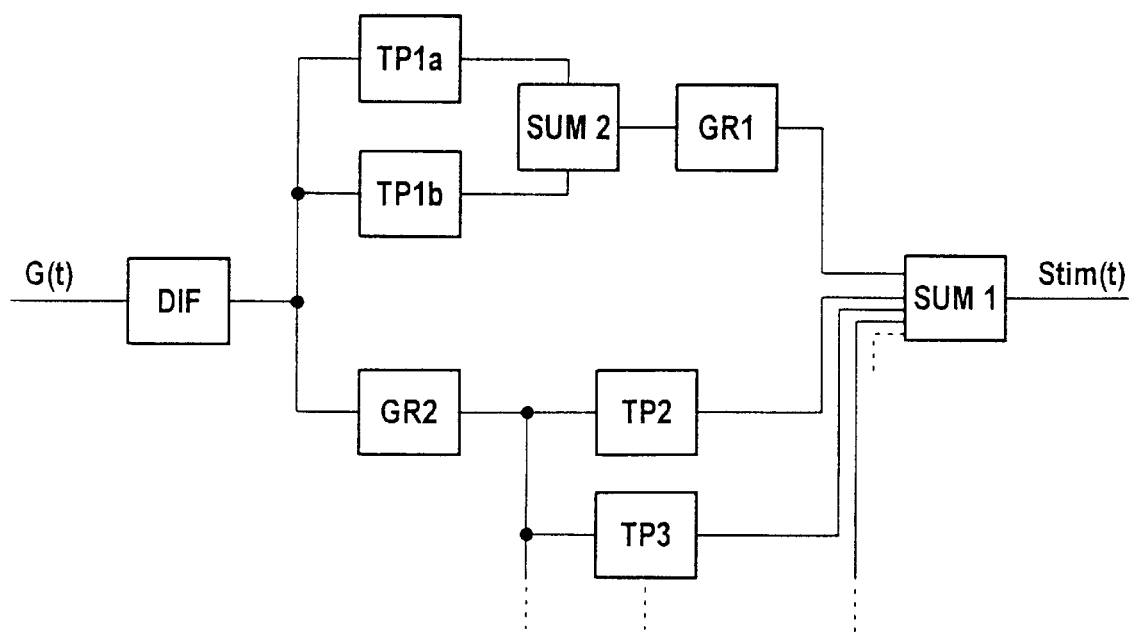
FIG. 9 is a block diagram of a second embodiment of an apparatus in accordance with the invention for conducting the inventive method.

FIG. 9 depicts an exemplary embodiment for generating a stimulation signal Stim(t) by means of which a refined simulation of the nerve stimulation is achieved. To this end, the low pass filtering of the low pass filter TP1 from FIG. 8 is implemented with two low pass filters TP1$a$ and TP1$b$, whose output signals are weighted and added by an adder SUM2. The output signal of SUM2 forms the input signal for the rectifier GR1. Furthermore, additional low pass filters TP3, etc. are arranged parallel to the low pass filter TP2. The output signals of the rectifier GR1 and of the low pass filters TP2, TP3, etc. are fed to the adder SUM1, wherein they are weighted and added. The low pass filter (or filters) TP3, etc. correspond to the circuit in FIG. 15.

The inventive method can be applied separately to each one of the three gradient coils, which respectively represent one physical gradient axis. If all three gradient coils are simultaneously switched (e.g. given tilted or rotated slices), however, then it can be inventively checked for each gradient axis whether or not a stimulation arises. This may not be sufficient, however, since a stimulation can be triggered, for example, by the simultaneous influence of all three gradient coils, although the stimulation threshold for each individual coil has not been exceeded. The check as to whether a stimulation can be triggered by the simultaneous influence of all three gradient coils can be easily realized with an additional step.

In this additional step, it is checked whether the following condition is satisfied (the additional indices relate to the observed respective physical gradient axes x,y,z):

$$[(\text{stim}_x(t)/\text{Stim}_{lim,x})^2+(\text{Stim}_y(t)/\text{Stim}_{lim,y})^2+(\text{Stim}_z(t)\text{Stim}_{lim,z})^2]^{1/2} < \text{Stim}_{factor},$$

where $\text{Stim}_{factor}$ designates the stimulation factor which describes the stimulation caused by the influence of all three gradient coils. For the stimulation factor, the inequality $\text{Stim}_{factor} \leq 1$ applies.

If the preceding condition is satisfied for each time t, then stimulations do not arise. If this condition is not satisfied, i.e. if the sum on the left side of the inequality is greater than the stimulation factor $\text{Stim}_{factor}$, then stimulations can be expected. The insertion of the stimulation factor $\text{Stim}_{factor}$ permits a greater flexibility in the adaptation of the inventive method to experimentally obtained data, which can be different for different MR devices.

Figure 20:
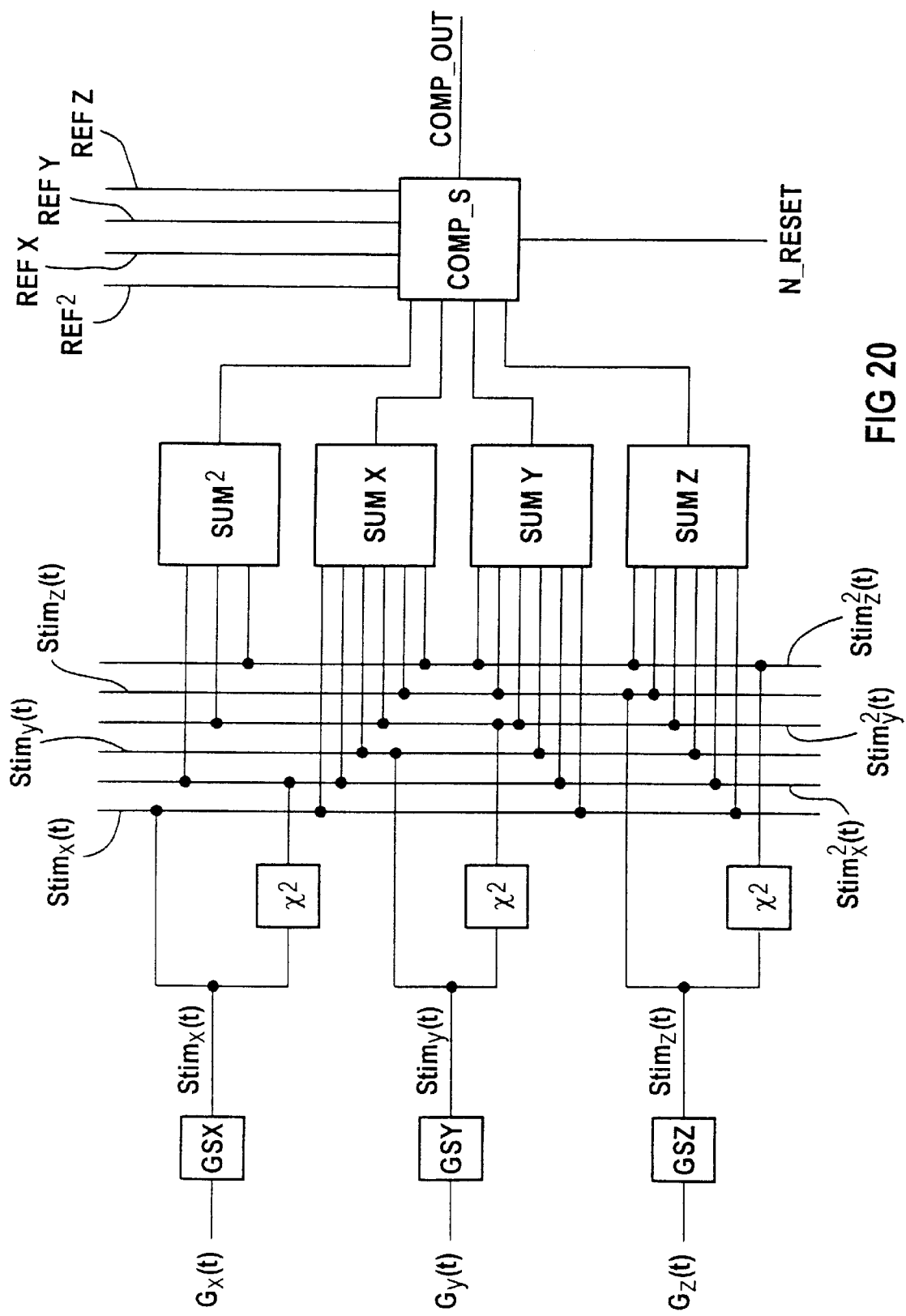
FIG. 20 is a more detailed circuit diagram of further embodiment of an apparatus in accordance with the invention for conducting the inventive method.

FIG. 20 depicts an exemplary embodiment a circuit of a device for conducting the method for three gradient coils of a gradient system. The input signals of the circuit are the gradient signals $G_x(t)$, $G_y(t)$ and $G_z(t)$ of the three physical gradient axes x, y and z. These are voltage signals. In one embodiment, these voltage signals are directly proportional to the currents in the gradient coils. The current real value signals, or target value signals, are suitable for this purpose, which signals are usually present as voltage signals in the gradient control and amplifier unit of the MR device. In another embodiment, without using the differentiator DIF in FIG. 8 and FIG. 9, voltage signals which are directly proportional to the first time derivative of a gradient coil current are used as gradient signals. As a rule, this type of signal is available as an output voltage $U_{out}(t)$ of the gradient control and amplifier unit. The voltage $U_{OUT}(t)$ is set such that the following equation applies: $U_{OUT}(t)=L \cdot di(t)/dt+R \cdot i(t)$. L is the inductance and R is the resistance of a gradient coil including its connecting cables, and i(t) is the gradient coil current. There is direct proportionality between the voltage $U_{OUT}(t)$ and the derivative of the gradient coil current di(t)/dt for R=0. In practice, the resistance R is not equal to zero. The error with which one is confronted when using the voltage signal $U_{OUT}(t)$ as the input signal is demonstrated in the following example: Given a resistance R of the gradient coil of 1 Ω, for example, which resistance has been increased by current displacement, and a current of 100 A, a voltage of 100 V drops at the resistance R. Given a total voltage of 1000 V, 900 V remain for the equation element L·di(t)/dt; the error would thus be 10%.

Figure 17:
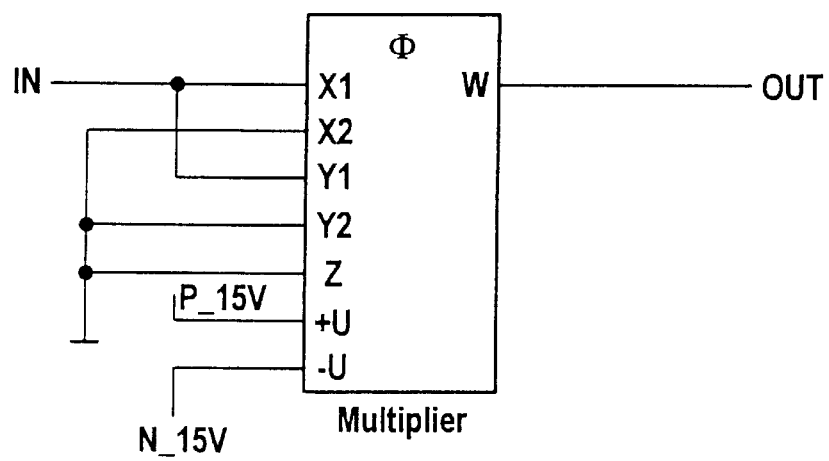

The gradient signals $G_x(t)$, $G_y(t)$ and $G_z(t)$ are fed respectively to the function blocks GSX, GSY and GSZ which correspond to the circuits, in FIG. 8 or FIG. 9. The output signals of these function blocks GSX, GSY and GSZ are the stimulation signals $\text{Stim}_x(t)$, $\text{Stim}_y(t)$ and $\text{Stim}_z(t)$, respectively. They are respectively fed to a squarer $x^2$ in one path. An example of a squarer circuit is given in FIG. 17, wherein a multiplier is configured as a squarer in that two connected inputs are fed the same input signal, and the three remaining inputs are connected to ground. This results in the following equation for the output voltage OUT of the squarer: OUT= IN·IN/10V. Given an input voltage IN of 10 V, the output voltage is likewise 10V.

Each stimulation signal $\text{Stim}_x(t)$, $\text{Stim}_y(t)$ and $\text{Stim}_z(t)$ is fed to a logic circuit directly as well as in squared form. The logic circuit is formed by four adders $SUM^2$, SUMX, SUMY and SUMZ, for example. The adder $SUM^2$ weights and adds the three squared stimulation signals. The combination of the three squared stimulation signals represents the stimulation in a rectangular three-dimensional coordinate system.

In the circuit according to FIG. 20, it is advantageous to square the stimulation signals directly, and not, as is explained in the description of the method, to first divide the stimulation signals by stimulation thresholds.

Since, as a rule, there is no longer rectangularity of the gradient field outside the examination region of the MR device, and the highest gradient field strength changes are achieved outside the examination region, the logic circuit contains three additional adders SUMX, SUMY and SUMZ, which respectively form the sum of all the linear and squared stimulation signals with a definable weighting. The weighting of the adder SUMX provides a high weighting of the signals related to the x-gradient-axis; the weighting of the adder SUMY provides a high weighting of the signals related to the y-gradient-axis, and the weighting of the adder SUMZ provides a high weighting of the signals related to the z-gradient-axis.

While the stimulation signals $\text{Stim}_x(t)$, $\text{Stim}_y(t)$ and $\text{Stim}_z(t)$ and their squared signals are always positive, their output signals are always negative, due to the sign inversion caused by the adders $SUM^2$, SUMX, SUMY and SUMZ.

The output signals of the adders $SUM^2$, SUMX, SUMY, SUMZ, are compared in a comparator circuit with storage unit COMP_S, to appertaining stored or supplied reference levels $REF^2$, REFX, REFY and REFZ. If at least one reference level is exceeded, then this indicates the attainment of a stimulation threshold, and a signal is continuously emitted at the message output COMP_OUT, thereby setting the output voltage of the gradient control and amplifier unit to zero in an online monitoring, for example. The signal at the message output COMP_OUT is cleared by a reset signal at the reset input N_RESET.

Figure 18:
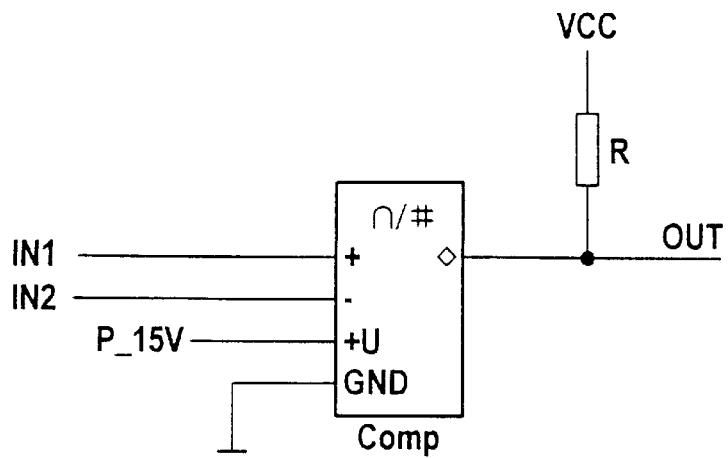

FIG. 18 depicts the basic function of a comparator COMP which combines two input signals IN1 and IN2 into one output signal. The signal output is thus located at a high level as long as IN1 is greater than IN2. If IN1 is smaller than IN2, the signal output is located at a low level.

Figure 19:
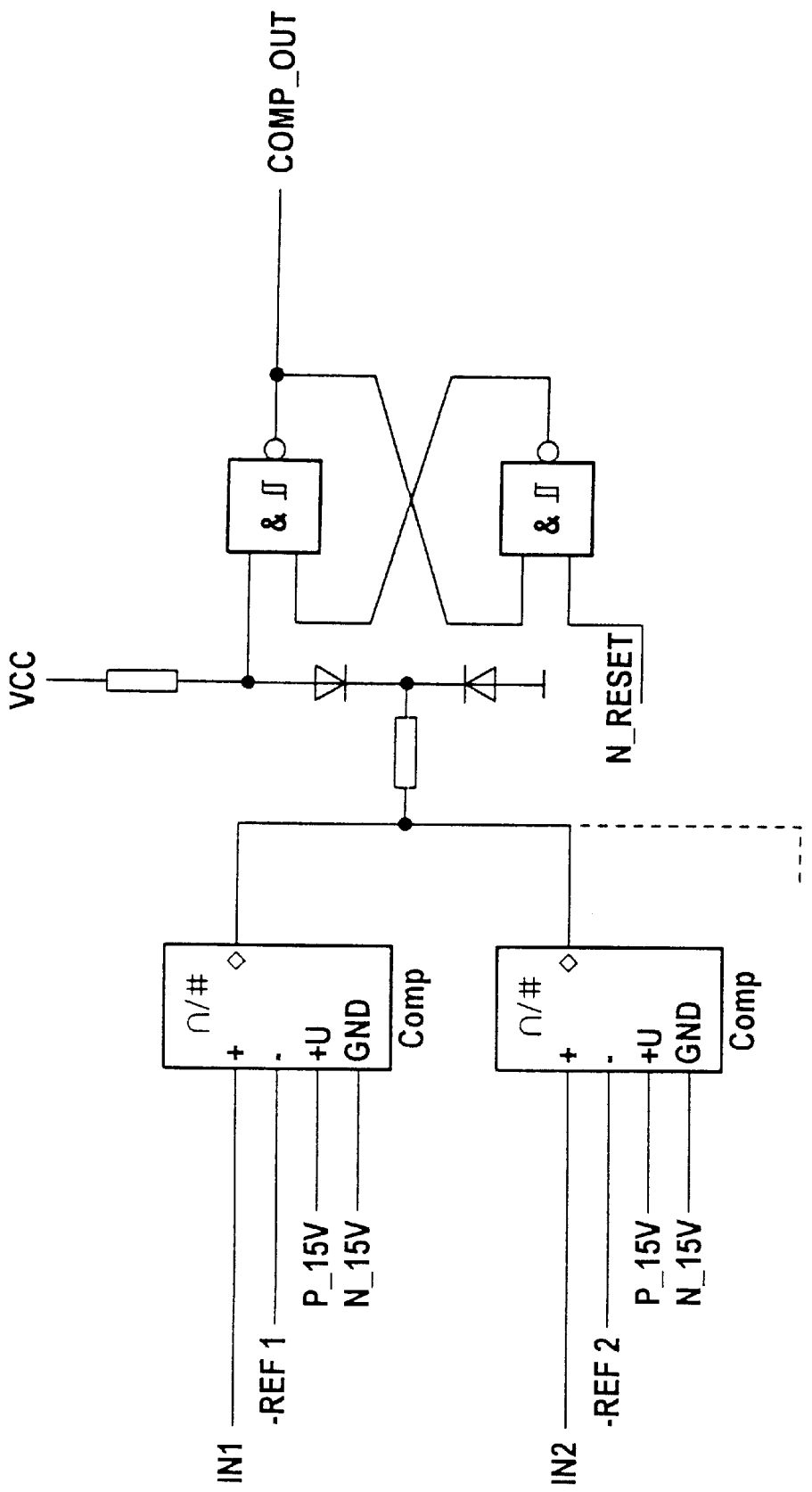

FIG. 19 depicts the comparator circuit with the storage unit COMP_S as a simple connection of comparators to a simple flip-flop consisting of two NAND gates as storage units. The comparator circuit COMP_S, contains comparators in accordance with the number of input signals. The resistance at VCC keeps the common open collector output of the comparators selected for this example at a high level. If, in one of the comparators, the input signal is more negative than the appertaining reference level, which is to be prescribed with a negative sign, then this comparator draws the common output of all comparators down to a low level and effectuates a high level at the output of the flip-flop, which leads to a stoppage of the measuring sequence, for example. This high level is maintained even if the comparator restores the common output of all comparators to the high level on the basis of the eliminated stimulation. Only a reset signal at the reset input N_RESET restores the flip-flop output to the low level again. Without the flip-flop, in an online monitoring, for example, the gradient control and amplifier unit would continue the stimulating measuring sequence subsequent to a short interruption. A time element can be used instead of the flip-flop, which element arrests the gradient control and amplifier unit until a measuring sequence break has been realized.

A squaring of the stimulation signals can be forgone if six sums are formed instead of the three squarers $X^2$ and adders $SUM^2$, SUMX, SUMY and SUMZ, which sums contain the following additional weightings in addition to the scalings corresponding to their stimulation portions:

$$\Sigma_{a1}(t) = Stim_x(t) + (\sqrt{2}-1) \cdot Stim_y(t) + (\sqrt{3}-\sqrt{2}) \cdot Stim_z(t)$$

$$\Sigma_{a2}(t) = Stim_x(t) + (\sqrt{2}-1) \cdot Stim_z(t) + (\sqrt{3}-\sqrt{2}) \cdot Stim_y(t)$$

$$\Sigma_{b1}(t) = Stim_y(t) + (\sqrt{2}-1) \cdot Stim_z(t) + (\sqrt{3}-\sqrt{2}) \cdot Stim_x(t)$$

$$\Sigma_{b2}(t) = Stim_y(t) + (\sqrt{2}-1) \cdot Stim_x(t) + (\sqrt{3}-\sqrt{2}) \cdot Stim_z(t)$$

$$\Sigma_{c1}(t) = Stim_z(t) + (\sqrt{2}-1) \cdot Stim_x(t) + (\sqrt{3}-\sqrt{2}) \cdot Stim_y(t)$$

$$\Sigma_{c2}(t) = Stim_z(t) + (\sqrt{2}-1) \cdot Stim_y(t) + (\sqrt{3}-\sqrt{2}) \cdot Stim_x(t)$$

This assumes that, given equally large gradients, the resulting gradient is greater than the individual gradient by $\sqrt{2}$ in the plane and by $\sqrt{3}$ in space. The worst case is covered by the assumption of three equally large gradients and by the transposition of the portions in the six sums.

The gradient field does not dynamically correspond exactly to the gradient coil current characteristic, since it is chronologically delayed and attenuated by eddy currents. If the reference level in the dynamic gradient filed is computed experimentally, then the abovementioned condition is already taken into account in the reference levels. If instead examinations are conducted in order to obtain the reference levels at static gradient fields, it is possible to evaluate the gradient coil current characteristic with eddy currents being taken into account. An evaluated gradient coil current signal is thus obtained, the characteristic of which corresponds to the actual dynamic gradient field.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for the simulation of an electrical stimulation in an examination subject generated by a gradient coil of a magnetic resonance device, comprising the steps of:

determining a gradient signal defined by a time characteristic of gradient pulses;

filtering said gradient signal with a filtering function lo form a filtered gradient signal;

forming, from said filtered gradient signal, a stimulation signal describing a degree of stimulation of said examination subject by said gradient pulse; and comparing said stimulation signal to a predetermined stimulation threshold and, if said stimulation signal exceeds said stimulation threshold, generating an indicator indicating that a stimulation which will be caused by said gradient pulse will exceed said stimulation threshold.

2. A method as claimed in claim 1 comprising the additional step of:

differentiating said gradient signal once with respect to time, prior to filtering said gradient signal, to obtain a differentiated gradient signal, and filtering said differentiated gradient signal, as said gradient signal, with said filtering function.

3. A method as claimed in claim 2 wherein said filtering function is a first filtering function and has a limit frequency, and wherein said filtered gradient signal is a first filtered gradient signal, and comprising the additional steps of:

additionally filtering said differentiated gradient signal with a second filtering function having a limit frequency which is lower than the limit frequency of said first filtering function, to obtain a second filtered gradient signal;

weighting said first filtered gradient signal and said second filtered gradient signal to obtain a first weighted and filtered gradient signal and a second weighted and filtered gradient signal, respectively; and forming said stimulation signal by logically combining said first weighted and filtered gradient signal and said second weighted and filtered gradient signal with a freely selectable logic operator.

4. A method as claimed in claim 3 comprising the additional steps of:

rectifying said first filtered gradient signal prior to weighting said first filtered gradient signal; and rectifying said differentiated gradient signal prior to filtering said differentiate gradient signal, as said gradient signal, with said second filtering function.

5. A method as claimed in claim 4 wherein at least one of the steps of filtering said gradient function with a first filtering function and filtering said gradient function with a second filtering function comprises convolving said gradient signal with an exponential function $$\frac{1}{\tau} e^{-\frac{t}{\tau}}$$

as at least one of said first filtering function and said second filtering function, wherein t represents time and wherein $\tau$ is a predetermined time constant.

6. A method as claimed in claim 5 wherein the step of filtering said gradient signal with said first filtering function comprises convolving said differentiated gradient signal with a first e-function $$G_{F1}(t) = G_{diff}(t) \otimes \frac{1}{T_1} e^{-\frac{t}{T_1}},$$

wherein $G_{F1}(t)$ is said first filtered gradient signal and wherein $G_{diff}(t)$ is said differentiated gradient signal; and wherein the step of filtering said gradient signal with said second filtering function comprising convolving said differentiated gradient signal with a second e-function $$G_{F2}(t) = \text{Abs}(G_{\text{diff}}(t)) \otimes \frac{1}{T_2} e^{-\frac{t}{T_2}},$$

wherein $G_{F2}(t)$ is said second filtered gradient signal and wherein $\text{Abs}(G_{\text{diff}}(t))$ is the rectified portion of said differentiated gradient signal.

7. A method as claimed in claim 4 wherein the step of weighting said first filtered gradient signal and said second filtered gradient signal comprises multiplying said first filtered gradient signal, after rectification thereof, by a predetermined first weighting factor, and multiplying said second filtered gradient signal by a predetermined second weighting factor.

8. A method as claimed in claim 7 comprising selecting a limit frequency for said first filtering function at a sufficiently high value for substantially eliminating a filtering effect of said first filtering function on said gradient signal, and selecting said second weighting factor sufficiently low for causing said second filtered and weighted gradient signal to produce substantially no contribution to logically combining said first filtered and weighted gradient signal and said second filtered and weighted gradient signal.

9. A method as claimed in claim 3 wherein the step of logically combining said first filtered and weighted gradient signal and said second filtered and weighted gradient signal comprises selecting a mathematical operator as said logic operator.

10. A method as claimed in claim 9 comprising adding said first filtered and weighted gradient signal to second filtered and weighted gradient signal.

11. A method as claimed in claim 1 comprising the additional steps of:
aborting imaging of an examination subject if and when said indicator is generated.

12. A method as claimed in claim 1 comprising the additional steps of:
prior to conducting said imaging using said pulse sequence, determining said stimulation signal associated with said pulse sequence; and
producing a message identifying that stimulation of said examination subject will occur.

13. A method as claimed in claim 1 wherein the step of filtering said gradient signal with said first filtering function comprises filtering said gradient signal by convolving said gradient signal and using an exponential function $$\frac{1}{\tau} e^{-\frac{t}{\tau}}$$

as said filtering function, wherein t represents time and $\tau$ is a predetermined time constant.

14. A method as claimed in claim 1 comprising selecting said stimulation threshold dependent on said examination subject.

15. A method as claimed in claim 1 wherein said magnetic resonance device comprises gradient coils respectively associated with three orthogonal axes x, y and z of a Cartesian coordinate system, and wherein the step of forming said stimulation signal comprises forming a stimulation signal $\text{Stim}_x(t)$ for said gradient coil associated with the x axis, forming a stimulation signal $\text{Stim}_y(t)$ for the gradient coil associated with the y axis, and forming a stimulation signal $\text{Stim}_z(t)$ for the gradient coil associated with the z axis, identifying respective stimulation limits $\text{Stim}_{\lim,x}$, $\text{Stim}_{\lim,y}$ and $\text{Stim}_{\lim,z}$, for each of said three axes, forming respective ratios $\text{Stim}_x(t)/\text{Stim}_{\lim,x}$, $\text{Stim}_y(t)/\text{Stim}_{\lim,y}$ and $\text{Stim}_z(t)/\text{Stim}_{\lim,z}$, for the respective axes, identifying a stimulation factor $\text{Stim}_{factor}$ describing a degree of stimulation caused by a combination of all of said gradient coils, and comparing said combination of all said ratios to said stimulation factor $\text{Stim}_{factor}$ and generating said indicator if said combination of all of said ratios exceeds said stimulation factor.

16. A method as claimed in claim 15 wherein the step of combining said ratios comprises squaring each of said ratios to obtain three squared ratios, and adding said three squared ratios and taking a square root of a sum of said three squared ratios, and wherein the step of comparing said ratios to said stimulation factor $\text{Stim}_{factor}$ comprises comparing said square root to said stimulation factor $\text{Stim}_{factor}$ and generating said indicator if said square root exceeds said stimulation factor $\text{Stim}_{factor}$.

17. A magnetic resonance imaging apparatus with a device for the simulation of electrical stimulations in an examination subject generated by at least one of the gradient coils of the apparatus, said device comprising:
a circuit having at least two parallel circuit paths;
a first of said two parallel paths comprising a series circuit of a first low pass filter stage followed by a first rectifier;
a second of said parallel paths comprising a series circuit of a second rectifier followed by a second low pass filter stage;
an input stage, connected to each of said first path and said second path, supplied with a gradient signal of said one of said gradient coils; and
an adder connected to respective outputs of said first path and said second path for weighting output signals from said first path and said second path to obtain weighted output signals and for adding said weighted output signals to form a stimulation signal describing the stimulation of said examination subject by said one of said gradient coils.

18. The device of claim 17 wherein said first low pass filter stage comprises a first low pass filter and a second low pass filter connected in parallel with each other and a first low pass filter stage adder, connected to each of said first and second low pass filters, for selectively weighting respective output signals from said first and second low pass filters and for adding the weighted output signals for supply to said adder as the output signal of said first of said signal paths.

19. The device of claim 17 wherein said second low pass filter stage comprises a first low pass filter and at least one second low pass filter connected in parallel with each other, with respective output signals of said first and second low pass filters being supplied to said adder as the output signal of said second of said signal paths.

20. The device of claim 17 wherein said input stage comprises a differentiator for differentiating said gradient signal of said one of said gradient coils.

21. The device of claim 17 wherein said input stage receives a current real value signal of a gradient control and amplifier unit.

22. The device of claim 17 wherein said input stage receives a current target value signal of a gradient control and amplifier unit.

23. The device of claim 17 wherein said input stage receives a signal from a gradient control and amplifier unit which is directly proportional to a first time derivative of a gradient coil current in said one of said gradient coils.

24. The device of claim 17 comprising a comparator unit with at least one comparator, supplied with said stimulation signal, which compares said stimulation signal to a predetermined reference level and which emits a message at a comparator unit output, indicating that stimulation of said examination subject has occurred, if said stimulation signal exceeds said reference level.

25. The device of claim 24 further comprising a storage module contained in said comparator unit, said module maintaining said message at said output of said comparator unit until receiving a reset signal.

26. The device of claim 24 further comprising a timer contained in said comparator unit which maintains said message at said output of said comparator unit for a predetermined time.

27. The device of claim 17 wherein said circuit is a first circuit supplied with a first gradient signal of a first of said gradient coils, and wherein said stimulation signal at said output of said first circuit is a first stimulation signal, and said device further comprising:

a second circuit, identical to said first circuit, supplied with a second gradient signal of a second of said gradient coils and having an output at which a second stimulation signal is present; and a further adder, supplied with said first stimulation signal and said second stimulation signal, for adding said first and second stimulation signals together with respective predetermined weightings for producing a further adder output, supplied to said comparator unit For comparison with said reference level as said stimulation signal.

28. The device of claim 17 wherein said circuit is a first circuit supplied with a first gradient signal of a first of said gradient coils, and wherein said stimulation signal at said output of said first circuit is a first stimulation signal, and said device further comprising:

a second circuit, identical to said first circuit, supplied with a second gradient signal of a second of said gradient coils and having an output at which a second stimulation signal is present;

a first squaring circuit, supplied with said first stimulation signal, for squaring said first stimulation signal to produce a squared first stimulation signal;

a second squaring unit, supplied with said second stimulation signal, for squaring said second stimulation signal for producing a squared second stimulation signal; and a further adder, connected between said first and second squaring units and said comparator unit, supplied with said squared first stimulation signal and said squared second stimulation signal for adding said squared first stimulation signal to said squared second stimulation signal with respectively predetermined weightings, for producing an output which is supplied to said comparator unit for comparison with said reference level as said stimulation signal.

29. The device of claim 17 further comprising:

a squaring unit supplied with said stimulation signal for squaring said stimulation signal to produce a squared stimulation signal;

a further adder, supplied with said stimulation signal and said squared stimulation signal for adding said stimulation signal to said squared stimulation signal with respective predetermined weightings, to produce a further adder output; and a comparator unit, supplied with said further adder output, for comparing said further adder output to a reference level and for emitting a message at a comparator unit output indicating that stimulation of said examination subject has occurred, if said further adder output exceeds said reference level.

* * * * *